(12) United States Patent
Yan et al.

(10) Patent No.: US 12,171,410 B2
(45) Date of Patent: Dec. 24, 2024

(54) ENDOSCOPE OBSERVATION WINDOW CLEANING

(71) Applicant: CANON U.S.A., INC., Melville, NY (US)

(72) Inventors: Ray Yan, Newton, MA (US); Seiji Takeuchi, Newton, MA (US)

(73) Assignee: Canon U.S.A., Inc., Melville, NY (US)

( * ) Notice: Subject to any disclaimer, the term of this patent is extended or adjusted under 35 U.S.C. 154(b) by 586 days.

(21) Appl. No.: 17/428,575

(22) PCT Filed: Feb. 5, 2020

(86) PCT No.: PCT/US2020/016750
§ 371 (c)(1),
(2) Date: Aug. 4, 2021

(87) PCT Pub. No.: WO2020/163449
PCT Pub. Date: Aug. 13, 2020

(65) Prior Publication Data
US 2022/0104696 A1 Apr. 7, 2022

Related U.S. Application Data

(60) Provisional application No. 62/801,553, filed on Feb. 5, 2019.

(51) Int. Cl.
*A61B 1/00* (2006.01)
*A61B 1/015* (2006.01)
(Continued)

(52) U.S. Cl.
CPC .......... *A61B 1/126* (2013.01); *A61B 1/00006* (2013.01); *A61B 1/00009* (2013.01);
(Continued)

(58) Field of Classification Search
CPC . A61B 1/126; A61B 1/00006; A61B 1/00011; A61B 1/0016; A61B 1/015; A61B 1/00091
See application file for complete search history.

(56) References Cited

U.S. PATENT DOCUMENTS

| | | | |
|---|---|---|---|
| 4,760,838 A | 8/1988 | Fukuda | |
| 5,575,756 A * | 11/1996 | Karasawa | A61B 1/0014 600/156 |

(Continued)

FOREIGN PATENT DOCUMENTS

| | | |
|---|---|---|
| KR | 10-2017-0092366 A | 8/2017 |
| WO | 2017/165511 A1 | 9/2017 |

OTHER PUBLICATIONS

Notification of Transmittal of the International Search Report and the Written Opinion of the ISA, and International Search Report and Written Opinion, for PCT/US2020/016750, dated Apr. 7, 2020.

*Primary Examiner* — Anh Tuan T Nguyen
*Assistant Examiner* — Rynae E Boler
(74) *Attorney, Agent, or Firm* — Canon U.S.A., Inc. IP Division

(57) ABSTRACT

One or more devices, systems, methods, and storage mediums for imaging and more particularly to minimally invasive medical devices, such as, but not limited to, spectrally encoded endoscopy (SEE), endoscopy, and/or other catheter-related apparatuses and systems, methods, and storage mediums for use with same, are provided herein. One or more devices, systems, methods and storage mediums may be for characterizing, examining and/or diagnosing, and/or measuring viscosity of, a sample or object in application(s) using an apparatus or system that includes, in one or more embodiments, an in-situ optics observation window or lens cleaning apparatus or system that provides a technique(s) for
(Continued)

cleaning the medical device optic(s) without removing the medical device during a surgical procedure.

15 Claims, 9 Drawing Sheets

(51) Int. Cl.
*A61B 1/06* (2006.01)
*A61B 1/12* (2006.01)

(52) U.S. Cl.
CPC ........ *A61B 1/00011* (2013.01); *A61B 1/0016* (2013.01); *A61B 1/015* (2013.01); *A61B 1/0655* (2022.02)

(56) References Cited

U.S. PATENT DOCUMENTS

| | | |
|---|---|---|
| 6,341,036 B1 | 1/2002 | Tearney et al. |
| 6,447,446 B1 | 9/2002 | Smith et al. |
| 7,341,556 B2 | 3/2008 | Shalman |
| 7,447,408 B2 | 11/2008 | Bouma et al. |
| 7,551,293 B2 | 6/2009 | Yelin et al. |
| 7,796,270 B2 | 9/2010 | Yelin et al. |
| 7,859,679 B2 | 12/2010 | Bouma et al. |
| 7,889,348 B2 | 2/2011 | Tearney et al. |
| 8,045,177 B2 | 10/2011 | Tearney et al. |
| 8,145,018 B2 | 3/2012 | Shishkov et al. |
| 8,838,213 B2 | 9/2014 | Tearney et al. |
| 9,254,089 B2 | 2/2016 | Tearney et al. |
| 9,295,391 B1 | 3/2016 | Tearney et al. |
| 9,415,550 B2 | 8/2016 | Tearney et al. |
| 9,557,154 B2 | 1/2017 | Tearney et al. |
| 9,846,940 B1 | 12/2017 | Wang |
| 9,869,820 B2 | 1/2018 | Chen et al. |
| 9,869,854 B2 | 1/2018 | Yamamoto |
| 10,095,020 B2 | 10/2018 | Tearney et al. |
| 10,194,065 B2 | 1/2019 | Takeuchi et al. |
| 10,222,607 B2 | 3/2019 | Wang |
| 10,234,694 B2 | 3/2019 | Wang et al. |
| 10,261,223 B2 | 4/2019 | Tearney et al. |
| 10,288,868 B2 | 5/2019 | Tearney et al. |
| 10,314,469 B1 | 6/2019 | Ikuta |
| 10,321,810 B2 | 6/2019 | Ikuta et al. |
| 10,337,987 B2 | 7/2019 | Wu et al. |
| 10,357,160 B2 | 7/2019 | Yamamoto et al. |
| 10,371,614 B2 | 8/2019 | Hosoda et al. |
| 10,401,610 B2 | 9/2019 | Ikuta et al. |
| 10,444,146 B2 | 10/2019 | Yamazoe et al. |
| 10,506,922 B2 | 12/2019 | Ikuta |
| 10,952,702 B2 | 3/2021 | Hamm et al. |
| 2009/0247831 A1 | 10/2009 | Miyamoto et al. |
| 2012/0316394 A1 | 12/2012 | Yoshida et al. |
| 2013/0172742 A1 | 7/2013 | Rankin et al. |
| 2015/0182108 A1* | 7/2015 | Fukuda .............. A61B 1/00091 600/157 |
| 2017/0238795 A1* | 8/2017 | Blumenkranz ........... B08B 3/02 |
| 2017/0290492 A1 | 10/2017 | Hamm et al. |
| 2017/0296038 A1* | 10/2017 | Gordon .............. A61B 1/00091 |
| 2017/0297536 A1* | 10/2017 | Giraud .............. G02B 27/0006 |
| 2017/0311789 A1* | 11/2017 | Mulcahey .............. A61B 1/126 |
| 2017/0360398 A1 | 12/2017 | Hamm et al. |
| 2018/0084981 A1 | 3/2018 | Wang |
| 2018/0088312 A1 | 3/2018 | Tsuji |
| 2018/0120555 A1 | 5/2018 | Ikuta et al. |
| 2018/0214008 A1 | 8/2018 | Yamazoe et al. |
| 2019/0110675 A1* | 4/2019 | Faria .............. G02B 23/2484 |
| 2019/0150720 A1 | 5/2019 | Altshuler et al. |
| 2019/0162977 A1 | 5/2019 | Koyama et al. |
| 2019/0172180 A1 | 6/2019 | Ganesan |
| 2019/0174038 A1 | 6/2019 | Takeuchi et al. |
| 2019/0223706 A1 | 7/2019 | Takeuchi et al. |
| 2019/0231182 A1 | 8/2019 | Brauer et al. |
| 2019/0254506 A1 | 8/2019 | Hamm et al. |
| 2019/0313975 A1 | 10/2019 | Dunfee et al. |
| 2020/0015663 A1* | 1/2020 | Kumagai ........... A61B 1/00135 |
| 2020/0100811 A1* | 4/2020 | Holsten ................. A61B 1/126 |

* cited by examiner

ENDOSCOPE OBSERVATION WINDOW CLEANING

CROSS-REFERENCE TO RELATED APPLICATION(S)

This application relates, and claims priority, to U.S. Prov. Patent Application Ser. No. 62/801,553, filed Feb. 5, 2019, the disclosure of which is incorporated by reference herein in its entirety.

FIELD OF THE INVENTION

The present disclosure relates generally to the field of imaging and more particularly to minimally invasive medical devices, such as, but not limited to, spectrally encoded endoscopy (SEE), endoscopy, and/or other catheter-using apparatuses and systems, and methods and storage mediums for use with same. Examples of SEE applications include imaging, evaluating and characterizing/identifying biological objects or tissue, such as, but not limited to, for gastrointestinal, cardio and/or ophthalmic applications. One or more devices, systems, methods and storage mediums may be for characterizing, examining and/or diagnosing, and/or measuring viscosity of, a sample or object in application(s) using an apparatus or system that includes, in one or more embodiments, an in-situ optics observation window cleaning apparatus or system that provides a technique for cleaning the medical device optic(s) without removing the medical device during a surgical procedure.

BACKGROUND OF THE INVENTION

Spectrally encoded endoscope (SEE) is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

A clear visualization is critical for endoscopic surgery. During surgery the endoscope observation lens or window may get fouled or soiled by blood, tissue, mucus, or other debris. The reduced visual acuity potentially reduces patient safety. Current typical cleaning methods rely on manual wiping by removing the scopes or using an irrigation system. Removing a scope during a surgery interrupts the procedure and increases the procedure duration and related risks. If an irrigation system is used to clean the windows, air tubes, water tubes or suction tubes bent towards the window surface may be used to flush away or suction away surgical debris from the windows. However, to direct the cleaning fluid onto the scope viewing window at the end, these irrigation, suction, and air/water tubes inside the endoscope often add significant Overall Diameter or Outer Diameter (OD) to the profile of the endoscopes and/or scope(s) thereof, or to an outer diameter of a nozzle. Such required structure or configuration adds to the cost and complexity of building, maintaining and using such endoscopes while also increasing the complexity of, and risks related to, using such endoscopes during a medical procedure(s). An increased Overall or Outer Diameter (OD) involves several disadvantages. For example, a relatively large diameter will limit or prohibit applications, which require a small or smaller diameter endoscope or device, because such large diameters result in a lack of accessibility in a patient and due to traumatizing that would result from trying to use such large diameters in a patient.

Accordingly, it would be desirable to provide at least one imaging (e.g., SEE, endoscopy, catheter-related, etc.) cleaning technique, storage medium and/or apparatus or system for use in at least one optical device, assembly or system to achieve efficient characterization and/or identification of biological object(s) or tissue, especially in a way that reduces or minimizes cost of manufacture and maintenance and/or in a way that reduces or minimizes overall diameter (and related costs). It would also be desirable to clean surgical viewing medical devices, such as endoscopes, in situ without the need of removing such medical device(s) from patients. In addition, if fluid is used to flush and clean the endoscope or medical device imaging or viewing windows, it would be desirable to achieve an apparatus, system and/or technique where an increase of scope OD by the fluid delivery channels preferably may be reduced and/or minimized and the cleaning efficiency may be increased and/or maximized by optimizing the cleaning flow.

SUMMARY OF THE INVENTION

Accordingly, it is also a broad object of the present disclosure to provide imaging apparatuses, systems, methods and storage mediums to the field of minimally invasive medical imaging devices, including, but not limited to, Spectrally Encoded Endoscopy (SEE), endoscopy, and other catheter-related devices. One or more embodiments of the present disclosure utilize a means to address the aforementioned issues of a fluid irrigation system and/or a manual wiping device or system. One or more embodiments of the present disclosure achieve a clear visualization of an operative field of the viewing window for a medical imaging device and/or a scope thereof, and may use different nozzles and/or channels to direct a cleaning flow to enhance the cleaning efficiency and cleanliness for a lens or window of the scope and/or medical imaging device.

It is also a broad object of the present disclosure to provide imaging (e.g., SEE, endoscopy, other catheter-related modalities, etc.) apparatuses and systems (e.g., using an apparatus or system for medical imaging or endoscope observation window cleaning), and methods and storage mediums for use with same, to achieve efficient and reduced/minimized OD while also increasing and/or maximizing cleaning efficiency and/or cleaning flow of such apparatuses and systems.

One or more embodiments of the present disclosure provide at least one imaging (e.g., SEE, endoscopy, other catheter-related modalities, etc.) cleaning technique, storage medium and/or apparatus or system for use in at least one optical device, assembly or system to achieve efficient characterization and/or identification of biological object(s) or tissue, in a way that reduces or minimizes cost of manufacture and maintenance and/or in a way that reduces or minimizes overall diameter (and related costs). One or more embodiments of the present disclosure achieve the ability to clean surgical viewing medical devices, such as endoscopes, in situ without the need of removing such medical device(s) from patients or objects/targets. In addition, if fluid is used to flush and clean the endoscope or medical device imaging or viewing windows in one or more embodiments of the present disclosure, such embodiments employ structure and/or techniques to avoid, reduce and/or minimize any increase of scope OD by the fluid delivery channels while increasing and/or maximizing cleaning efficiency, such as, but not limited to, by optimizing cleaning flow. Indeed, the embodiments of the present disclosure achieve an efficient way or ways to clean viewing window(s) for one or more medical devices, such as, but not limited to, endoscopes.

In accordance with one or more embodiments of the present disclosure, SEE apparatuses and systems, and methods and storage mediums may operate to characterize tissue type in addition to providing a morphological image to help an operator's diagnostic decision based on quantitative tissue information. In accordance with one or more embodiments of the present disclosure, SEE apparatuses and systems, and methods and storage mediums may operate to characterize biological objects other than tissue. For example, the characterization may be of a biological fluid such as blood or mucus.

In one or more embodiments of the present disclosure, a window cleaning nozzle may be used, where the window cleaning nozzle has a through hole opening to expose an observation window without impairing a field of view of a scope at the same time to position the scope on radial and/or axial direction(s) relative to a tube (e.g., an outer tube).

In one or more embodiments, an imaging apparatus may include: a probe or scope having at least one signal transmitting element, a proximal end with a signal transmitting connector, and a distal end operating to communicate a probing signal with a specimen, object, or target at an imaging location to generate an image, the distal end of the probe or scope operating to connect to or include an imaging or observation window or lens; and a nozzle having a through hole or a center hole opening to expose the imaging or observation window or lens, and having one or more grooves that operate to clean the imaging or observation window or lens of the probe or scope at the imaging location.

One or more embodiments may have one or more of the following: (i) apparatus further including an outer tube or outer tubular sheath; (ii) the nozzle operating to expose the imaging or observation window or lens without impairing a field of view of the probe or scope; (iii) the nozzle operating to position the probe or scope on both radial and axial directions relative to the outer tube or outer tubular sheath; and/or (iv) the one or more grooves being connected to an annular fluid delivery channel for cleaning of the window or lens, the annular fluid delivery channel being formed or defined between the probe or scope and the outer tube or outer tubular sheath and the annular fluid delivery channel operating to reduce or minimize an outer diameter of the apparatus.

One or more embodiments may have one or more of the following: (i) the one or more grooves being disposed on a proximal surface of the nozzle; (ii) the one or more grooves being perpendicular or substantially perpendicular to an axis extending along a length of the nozzle; (iii) the proximal surface being perpendicular or substantially perpendicular to an axis extending along a length of the nozzle; (iv) the one or more grooves operating to become or define one or more closed channels for cleaning fluid in a case where the nozzle is attached to a distal end of the outer tube and the scope or probe is inserted into the center hole or through hole of the nozzle; (v) the one or more grooves on the nozzle being angled with respect to a radial direction of the nozzle proximal surface; (vi) the one or more grooves being arranged peripherally around the through hole or the center hole of the nozzle; (vii) in a case where the cleaning fluid is delivered into and/or through the one or more grooves, the one or more grooves operating to guide the fluid in a direction to flush at least one surface of the window or lens and to facilitate formation of a vortex and/or swirl type of flow on the at least one surface of the window or lens to enhance cleaning efficiency; (viii) the one or more grooves operating to guide the fluid in a direction to flush the at least one surface of the window or lens tangentially and to facilitate formation of a vortex and/or swirl type of flow on the at least one surface of the window or lens to enhance cleaning efficiency; and/or (ix) the nozzle having one or more channels to deliver and direct the fluid to provide both window or lens cleaning and one or more irrigation functions to increase procedural efficiency by eliminating device exchange(s).

One or more embodiments may have one or more of the following: (i) the one or more grooves including at least one helical groove on an inner surface of the nozzle along the axial direction of the nozzle; (ii) the at least one helical groove communicating with the fluid channel between the outer tube and the probe or scope to deliver the fluid to the at least one surface of the window or lens; (iii) the at least one helical groove operating to become or define one or more closed helical channels for the cleaning fluid in a case where the nozzle is attached to the distal end of the outer tube and the scope or probe is inserted into the center hole or the through hole of the nozzle; (iv) the distal surface of the nozzle being aligned flush with the at least one surface of the window or lens; (v) in a case where the cleaning fluid exits the one or more closed helical channels, a fluid flow velocity having a velocity component in the axial direction of the nozzle and also has a velocity component with in a plane of the at least one surface of the window or lens in a tangential direction of the at least one surface of the window or lens, which facilitates a formation of a vortex flow on the at least one surface of the window or lens to enhance cleaning efficiency; (vi) the nozzle being an individual component or a part of the outer tube at a tip of the tube; and/or (vii) the axial fluid flow velocity being used for irrigation.

One or more embodiments may have one or more of the following: (i) the number of the one or more grooves is $\geq 1$; (ii) an angle, $\theta$, of the one or more grooves with respect to the axial direction of the nozzle meets the following equation or condition: $0° <= \theta < 90°$; and/or (iii) the angle, $\theta$, is $=0°$, at which the one or more grooves are straight and parallel or substantially parallel to the nozzle axis.

One or more embodiments may have one or more of the following: (i) the at least one signal transmitting element is at least one rotatable signal transmitting element; (ii) the rotatable signal transmitting element of the probe includes or comprises fiber; (iii) the apparatus further includes a rotary joint operating to transmit signals between a stationary portion of the apparatus and the at least one rotatable signal transmitting element of the probe or scope; (iv) the apparatus further includes a driving motor that operates to one or more of: (a) drive the rotary joint to drive rotational and/or axial movement of the probe or scope; and (b) control an angular position of the rotary joint; (v) the apparatus further includes the stationary portion of the apparatus, wherein the stationary portion comprises a signal source and one or more signal detector subsystems; and/or (vi) the rotary joint includes a stationary portion and a rotary portion.

One or more embodiments may include at least one processor that operates to: (i) acquire the probing signal to generate the image; and (ii) to control fluid(s) and/or cleaning fluid via the nozzle and/or the one or more grooves to clean the window or lens and/or to provide one or more irrigation function(s).

In one or more embodiments, the imaging location may be located inside the specimen, object, or target such that the cleaning occurs in situ in the specimen, object, or target.

In one or more embodiments, the nozzle further operates to provide one or more irrigation function(s) as well as operating to clean the imaging or observation window or lens of the probe or scope. The nozzle may further include one or more channels to deliver and direct fluid(s) and/or cleaning fluid to provide both the window or lens cleaning and the one or more irrigation functions to increase procedural efficiency by eliminating device exchange(s).

The one or more channels may one or more of the following: (i) communicate with the one or more grooves to deliver and direct the fluid and/or cleaning fluid; (ii) extend from a proximal end surface of the nozzle to an outer diameter surface of the nozzle and operate to allow outwards flow for the one or more irrigation function(s); (iii) have a plurality of portions that are differently sized and/or shaped to provide different flow velocities for the cleaning and/or the one or more irrigation function(s); (iv) include one or more exits or through holes extending from the channel to a distal end surface of the nozzle to provide outward and forward liquid flow channels for the one or more irrigation function(s); and/or (v) include one or more exits or through holes extending from the channel to an outer diameter surface of the nozzle to provide outward liquid flow channels for the one or more irrigation function(s). The one or more channels may include: (i) one or more exits or through holes extending from the channel to a distal end surface of the nozzle to provide outward and forward liquid flow channels for the one or more irrigation function(s); and (ii) include one or more exits or through holes extending from the channel to an outer diameter surface of the nozzle to provide outward liquid flow channels for the one or more irrigation function(s). The one or more channels may include: (i) one or more exits or through holes extending from the channel to a distal end surface of the nozzle to provide outward and forward liquid flow channels for the one or more irrigation function(s); and (ii) extend from a proximal end surface of the nozzle to an outer diameter surface of the nozzle and operate to allow outwards flow for the one or more irrigation function(s).

In one or more embodiments, (i) the number of the one or more grooves is $\geq 1$; and (ii) a distance, D, between a center of each groove of the one or more grooves and an axis extending along a length of the nozzle may meet the following equation: $0<D<R+W/2$, where a width, W, of the each groove of the one or more grooves is $0<W<R$, where R is a radius of a center hole of the nozzle.

One or more embodiments may employ an annular fluid delivery channel between a scope and an outer tube to reduce and/or minimize (or avoid an increase to) the OD of the overall profile of the medical imaging device and/or scope thereof.

In one or more additional embodiments, peripherally distributed grooves may be used on a proximal surface of a nozzle to direct the cleaning flow onto the viewing or window surface tangentially or substantially tangentially to facilitate formation of a vortex and/or swirl type of flow on the viewing or window surface to enhance the cleaning efficiency.

In one or more further embodiments using a nozzle, the nozzle may have channels to deliver and direct fluid flow providing window cleaning and/or irrigation functions to increase or maximize procedural efficiency by eliminating one or more device exchanges.

In one or more embodiments of the present disclosure, it is possible to, in imaging (e.g., SEE, endoscopy, other catheter-related imaging, etc.), reduce the size of the optical apparatus and/or system and acquire black and white and/or color images.

According to other aspects of the present disclosure, one or more additional apparatuses, one or more systems, one or more methods, and one or more storage mediums using observation window cleaning structure(s) and/or technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE EMBODIMENTS

Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope; arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus. The endoscope may include or use spectrally encoded endoscopy (SEE), Optical Coherence Tomography (OCT), a chip-on-tip camera, etc.

One or more devices, optical systems, methods, and storage mediums for obtaining a direct image (e.g., black and white, color, etc.) of a subject, such as tissue, using an imaging technique, a window or lens cleaning technique, and/or for diagnosing, irrigating, suctioning, dilating (e.g., balloon), culturing, tissue sampling, performing a biopsy, implanting a drug and/or performing any other type of diagnosis and/or treatment using an imaging technique are disclosed herein. In accordance with at least one aspect of the present disclosure, one or more devices, optical systems, methods, and storage mediums discussed herein use an imaging feature, function or technique; and one or more cleaning feature(s), function(s), technique(s) and/or structure(s).

Figure 1:
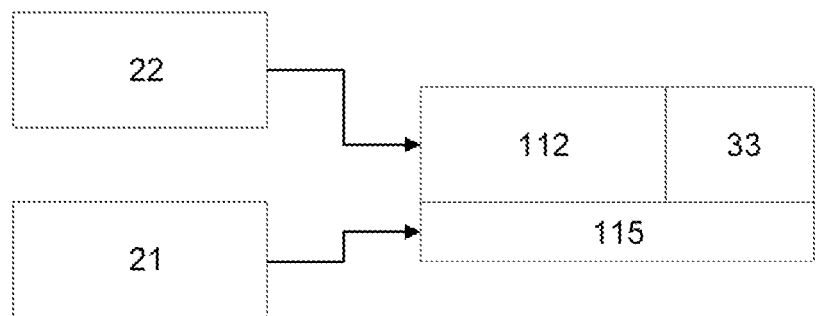
FIG. 1 shows a schematic diagram of at least one embodiment of a medical imaging device or system including a window cleaning apparatus or system in accordance with one or more aspects of the present disclosure.
Figure 2:
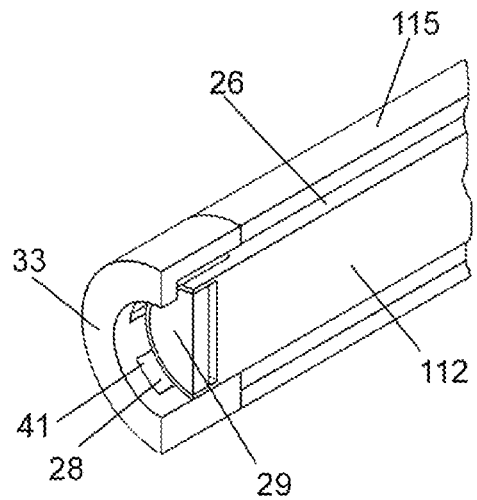
FIG. 2 shows at least one embodiment of a medical imaging device scope assembly with one or more window cleaning fluid channels in accordance with one or more aspects of the present disclosure.
Figure 3:
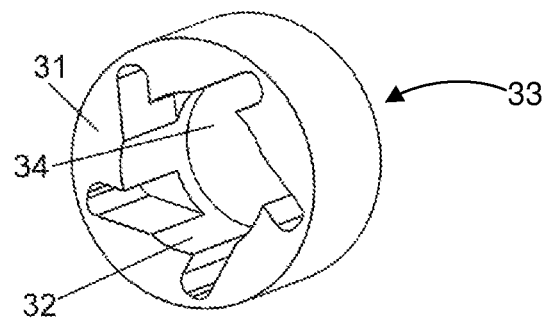
FIG. 3 shows at least one embodiment of a nozzle with built-in grooves that may be used in a medical imaging device in accordance with one or more aspects of the present disclosure.
Figure 4:
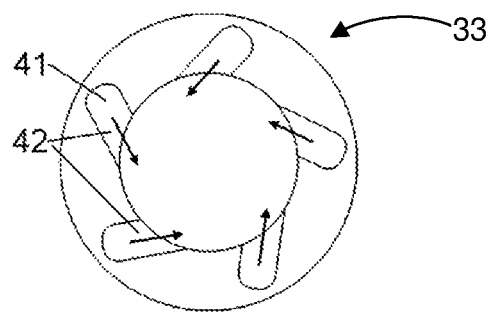
FIG. 4 shows a proximal side view of at least one embodiment of a nozzle with built-in grooves for fluid channels that may be used in a medical imaging device in accordance with one or more aspects of the present disclosure.

In one or more embodiments, one or more cleaning technique(s) and/or structure(s) may be used to achieve a clear visualization of an operative field of the viewing window for a medical imaging device and/or a scope thereof, and one or more embodiments may use different nozzles and/or channels to direct a cleaning flow to enhance the cleaning efficiency and cleanliness for a lens or window of the scope and/or medical imaging device. One or more systems, devices, methods and storage mediums are provided herein, including, but not limited to, the embodiment as shown in FIG. 1. FIG. 1 shows at least one embodiment example of a medical imaging apparatus and/or system (e.g., an endoscopy system, an SEE system, etc.). In one or more embodiments, an apparatus or system may use an optical/imaging and control system 22 and a fluid supply system 21 as diagrammatically shown in FIG. 1. One or more embodiments of the optical/imaging and control system 22 may be used, including, but not limited to, one or more features of the present disclosure as discussed herein (see e.g., imaging details of apparatus/system 100 in FIG. 16 and as discussed below, one or more details of FIGS. 16-19 and as discussed below, imaging or control details as discussed below, etc.). In one or more embodiments, an apparatus or system for delivery of fluid (e.g., at least one embodiment of the fluid supply system 21) for an imaging (e.g., of or by an endoscope) window (e.g., an endoscope observation window) or lens (see e.g., a window or lens 29 in FIG. 2) cleaning may include an endoscope or other medical imaging device having a scope 112, an outer tube 115 (e.g., an outer hollow tube, other hollow geometric structure, etc.), a nozzle 33 with a through hole opening that operates to expose the window (e.g., an observation window) or lens without impairing a field of view of the scope (see e.g., FIGS. 1-2). As shown in FIGS. 1-2, an annular fluid delivery channel 26 (and/or other fluid delivery means) for window or lens cleaning may be formed between the scope 112 and the outer tube 115 (e.g., an outer hollow tube, other hollow geometric structure, etc.). In one or more embodiments, the nozzle 33 may position the scope 112 on both radial and axial directions relative to the outer tube 115. In one or more embodiments, grooves 41 may be disposed on a proximal surface 31 of a nozzle 33 (e.g., a cleaning nozzle 33 as shown in one or more of FIGS. 1-3) of the scope 112 and/or the imaging device (see e.g., the device or system diagrammatically shown in FIG. 1, the apparatus/system 100 shown in FIG. 16, etc.), and the grooves 41 may be perpendicular or substantially perpendicular to an axis (e.g., an axis extending longitudinally through the nozzle 33, an axis extending along a length of the nozzle 33, etc.) of the nozzle 33. In one or more embodiments, the proximal surface 31 of the nozzle 33 may be perpendicular or substantially perpendicular to an axis (e.g., an axis extending longitudinally through the nozzle 33, an axis extending along a length of the nozzle 33, etc.) of the nozzle 33. In a case where the nozzle 33 is attached to a distal end of an outer tube 115 and a distal end of the scope 112 is inserted into and fit with a center hole or the through hole (see e.g., a nozzle fitting surface 32 to fit the nozzle 33 with an outer diameter (OD) of the scope 112, a nozzle fitting surface 32 to receive therein or fit the scope 112 therein, etc.) of the nozzle 33, the one or more grooves 41 may become or define one or more closed channels (see e.g., fluid exits 28 and/or the grooves 41 being disposed near and/or connected to the fluid channel 26) that operate to allow cleaning fluid to flow there though (e.g., from the fluid channel 26 between the scope 112 and the outer tube 115) (see e.g., as shown in FIG. 2). In one or more embodiments, one or more of the grooves 41 on the nozzle 33 may be angled with respect to the nozzle surface radial direction (see e.g., FIGS. 3-4). The one or more grooves 41 may be arranged peripherally around a center hole or the through hole 34 of the nozzle 33. In a case where cleaning fluid is delivered into the one or more grooves 41, the one or more grooves 41 may operate to: (i) guide or define the fluid direction to flush at least one surface of the window or the lens 29 (e.g., tangentially flush the at least one surface of the window or the lens 29), and (ii) facilitate formation of a vortex and/or swirl type of flow on the at least one surface of the window or the lens 29 to enhance the cleaning efficiency (see one or more dimension and directional details of FIG. 4). In at least the embodiment of FIG. 4, arrows 42 show the cleaning fluid flow exiting directions from the grooves 41 of the nozzle 33.

Figure 5:
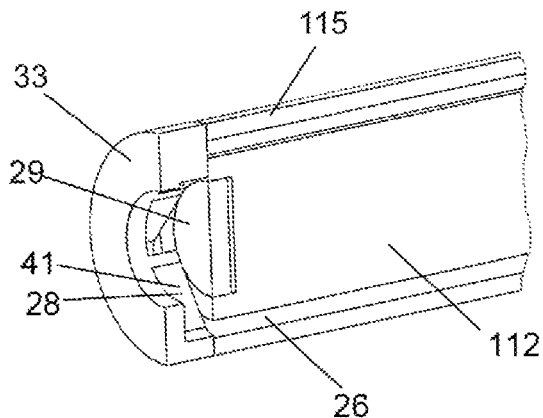
FIG. 5 shows at least one additional embodiment of a medical imaging device scope assembly with one or more window cleaning fluid channels in accordance with one or more aspects of the present disclosure.

In one or more embodiments, as shown in FIG. 5, the distal end of the outer tube 115 (e.g., a tubular outer tube, such as the tube 115 embodiment in FIG. 5) may be aligned flush with the distal end of the scope 112. In one or more embodiments, the scope 112 may not be inserted into the center hole or the through hole 34 of the nozzle 33. The nozzle 33 may be attached to the distal end of the outer tube 115 and the scope 112 to position the scope 112 relatively to the outer tube 115.

Figure 6:
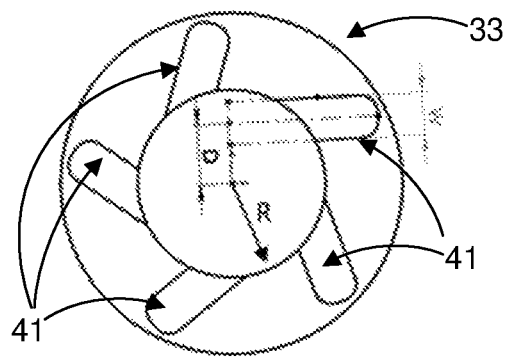
FIG. 6 shows at least one embodiment of a nozzle with built-in grooves for fluid channels along with one or more dimension details that may be used in a medical imaging device in accordance with one or more aspects of the present disclosure.

In one or more additional embodiments, the one or more grooves 41 may have different nozzle groove designs including the number of grooves (see e.g., five grooves 41 in the one or more embodiments of FIGS. 3-11 and 15, four grooves 41' in the one or more embodiments of FIGS. 12-14, etc.) and different dimensions of the grooves, such as, but not limited to, the embodiment example shown in FIG. 6. For example, the number of the grooves on the nozzle is preferably equal to or greater than (1. In one or more embodiments, the distance, D, between the groove center and the nozzle axis (e.g., an axis extending perpendicularly or transversely through the center of the nozzle 33, an axis extending laterally through the center of the nozzle 33, an axis that is collinear or coplanar with the center of the nozzle 33, etc.) preferably meets the following equation: 0<D<R+W/2, where a groove width, W, is 0<W<R. As shown in FIG. 6, R is a radius of a center hole (e.g., the hole 34) of the nozzle 33. The number of grooves and one or more of the dimensions or any other structural detail of the groove may be variable, and may change from one embodiment to another embodiment and/or from one groove to another groove. Such structural detail of one or more grooves are not limited to the details shown in the FIGS. for the grooves 41, grooves 41', etc., and one or more embodiments may have structure or shape different from any detail shown in the FIGS. and/or as discussed herein.

Figure 7:
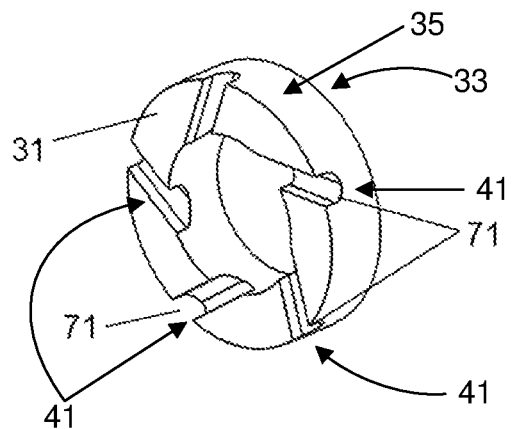
FIG. 7 shows a perspective view of at least one embodiment of a nozzle with built-in grooves in accordance with one or more aspects of the present disclosure.

In one or more embodiments, one or more of the nozzle grooves 41 may operate to both perform window or lens cleaning and irrigation fluid delivery. As shown in FIG. 7, the grooves 41 on the nozzle proximal end surface 31 are cut through and reach out to the OD surface or outer surface 35 of the nozzle 33, which allow outwards fluid flow from the nozzle outer surface 35 to provide an irrigation function (e.g., such cut through openings operate as exits 71 for irrigation flow in one or more embodiments).

In one or more embodiments, the nozzle 33 may have channels to deliver and direct fluid flow providing window cleaning and/or irrigation functions to increase or maximize procedural efficiency by eliminating one or more device exchanges.

Figure 8:
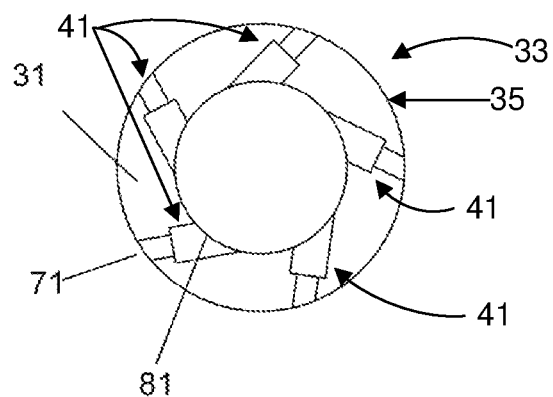
FIG. 8 shows at least one embodiment of a nozzle with built-in grooves having exits for irrigation flow in accordance with one or more aspects of the present disclosure.
Figures 9A, 9B:
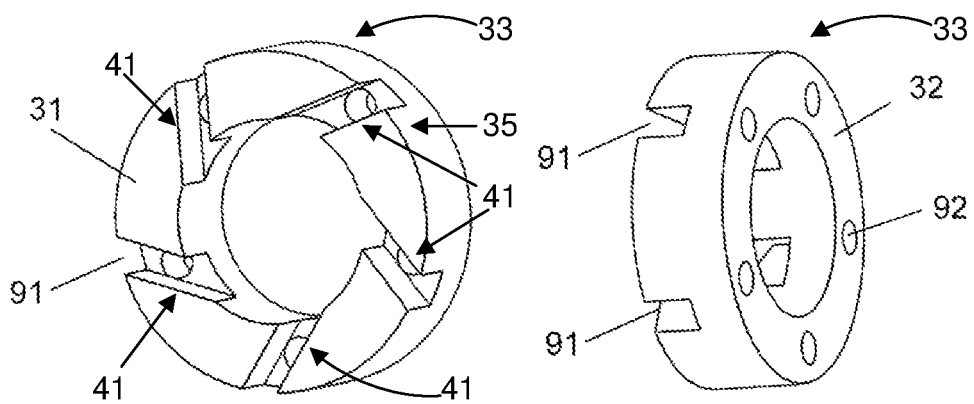
FIGS. 9A-9B show two views, one in FIG. 9A and one in FIG. 9B, of at least one embodiment of a nozzle with built-in grooves used for both window cleaning and irrigation fluid delivery in accordance with one or more aspects of the present disclosure.
Figure 10:
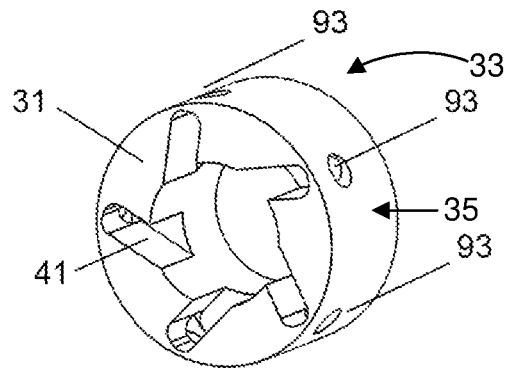
FIG. 10 shows at least one additional embodiment of a nozzle with built-in grooves having exits for irrigation flow in accordance with one or more aspects of the present disclosure.
Figures 11A, 11B:
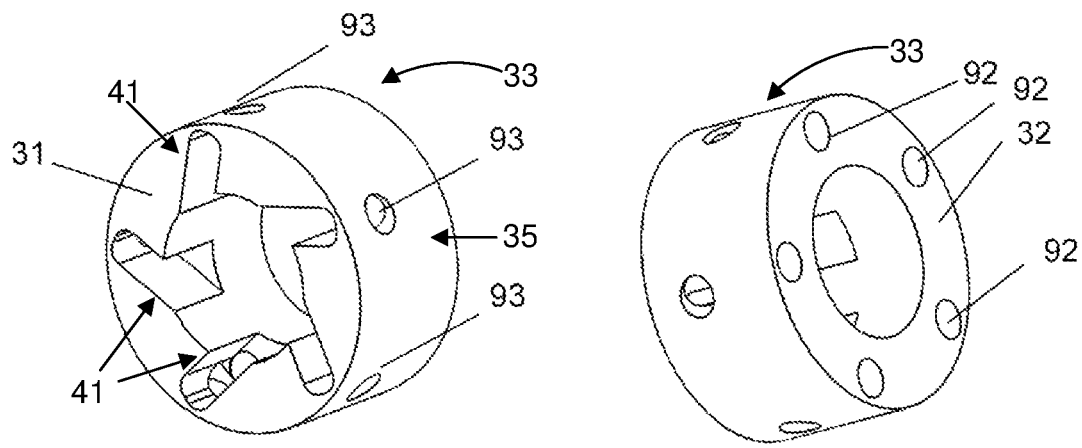
FIGS. 11A-11B show two views, one in FIG. 11A and one in FIG. 11B, of at least one additional embodiment of a nozzle with built-in grooves having exits for irrigation flow in accordance with one or more aspects of the present disclosure.

As aforementioned, one or more of the nozzle grooves (e.g., the grooves 41 discussed above, the grooves 41' discussed below, etc.) may operate to both perform window or lens cleaning and irrigation fluid delivery. In one or more further embodiments, such as, but not limited to the embodiment example shown in FIG. 8, such structural attributes may be achieved with different structure. For example, the groove 41 channels on the nozzle proximal end surface 31 may reach out to the OD surface (or outer surface 35 of the nozzle 33) with differently sized grooves (e.g., the one or more grooves may be differently sized along the nozzle 33, multiple stacked grooves that are differently sized may be used, grooves 41 having two or more portions with different dimensions (e.g., width, length, etc.) as shown in FIG. 8, etc.). The different orifice sizes for the openings or exits 71 of outwards irrigation flow versus the openings or exits 81 of inwards window cleaning flow result in different flow velocities according to one or more irrigation and cleaning requirements as desired in one or more embodiments.

As aforementioned, one or more of the nozzle grooves 41 may operate to both perform window or lens cleaning (e.g., on one or more sides of the lens 29, etc.) and irrigation fluid delivery. In one or more further embodiments, such as, but not limited to the embodiment example shown in FIGS. 9A-9B, such structural attributes may be achieved with different structure. For example, the grooves 41 on the nozzle proximal end surface 31 may be cut through and reach out to the OD surface (or the outer surface 35 of the nozzle 33) as shown via openings, cuts, or apertures 91. There also may be through holes 92 in each groove 41 going through the nozzle 33 from the proximal end 31 (see e.g., FIG. 9A) to the distal end 32 (or from the groove 41 surface to the distal end surface 32 of the nozzle 33, etc.) (see e.g., FIG. 9B). These features allow the fluid to form jetting flows outwards and forwards from at least both the nozzle outer surface 35 and distal end surface 32 to provide at least one irrigation function.

As aforementioned, one or more of the nozzle grooves (see e.g., the grooves 41, the grooves 41' discussed below, etc.) may operate to both perform window or lens cleaning and irrigation fluid delivery. In one or more further embodiments, such as, but not limited to the embodiment example shown in FIG. 10, such structural attributes may be achieved with different structure. For example, there may be holes 93 in each groove 41 from the groove apex (or a portion of the groove that contacts an outer surface 35 or an OD surface of the nozzle 33) through the nozzle 33 wall along the groove direction. These holes allow the fluid in the nozzle grooves 41 to flow outwards from the nozzle outer surface 35 to provide at least one irrigation function.

As aforementioned, one or more of the nozzle grooves (e.g., the grooves 41, the grooves 41' discussed below, etc.) may operate to both perform window or lens cleaning and irrigation fluid delivery. In one or more further embodiments, such as, but not limited to the embodiment example shown in FIGS. 11A-11B, such structural attributes may be achieved with different structure. For example, the grooves 41 on the nozzle proximal end surface 31 may be cut through and reach out to the OD surface (or the outer surface 35 of the nozzle 33). There also may be through holes 92 in each groove 41 going through the nozzle 33 from the proximal end 31 to the distal end 32, from a surface of the groove 41 to the distal end 32 of the nozzle 33, etc. One or more embodiments may include through holes 93 in each groove 41 as aforementioned (see e.g., FIGS. 11A-11B). These features allow the fluid to form jetting flows outwards and forwards from both the nozzle outer surface 35 and distal end surface 32 and/or the groove(s) 41 to provide at least one irrigation function.

Figure 12:
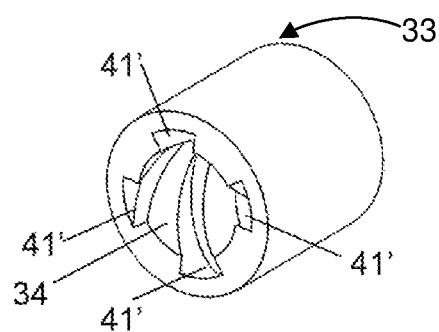
FIG. 12 shows at least one embodiment of a nozzle with helical grooves in accordance with one or more aspects of the present disclosure.
Figure 13:
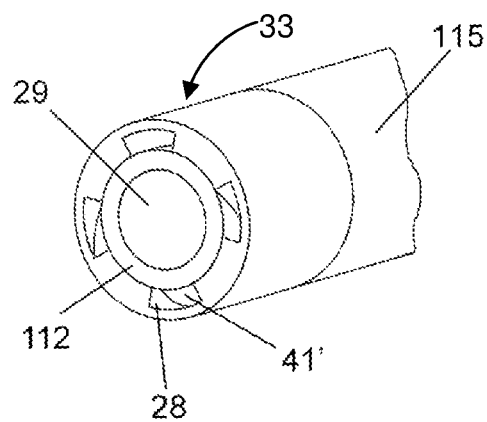
FIG. 13 shows at least one embodiment of a nozzle with helical grooves having a nozzle distal surface aligned flush with a scope window surface in accordance with one or more aspects of the present disclosure.

In one or more additional embodiments (e.g., as shown in at least FIGS. 12-13), a nozzle 33 may have one or more helical grooves 41' (which may have the same or similar features as one or more of the aforementioned grooves 41, but is labeled as 41' to indicate that the grooves 41' of this embodiment include a helical structure) on its Internal or Inner Diameter (ID) surface along the axial direction (see e.g., FIG. 12). The one or more helical grooves 41' may communicate with the fluid channel 26 between the outer tube 115 and the scope 112 to deliver fluid to at least one surface of the distal window or lens 29. The one or more grooves 41' preferably may become or define closed channels for the cleaning fluid in a case where the nozzle 33 is attached to the distal end of the outer tube 115 and the scope 112 is inserted into the center hole or the through hole 34 of the nozzle 33. Preferably, the nozzle distal surface 32 is aligned flush with a surface of the window or lens 29 of the scope 112 as best seen in FIG. 13. When or in a case where the window or lens cleaning fluid exits the helical channels (e.g., the grooves 41' and/or the fluid exists 28), the fluid flow velocity has not just the velocity component in the axial direction, but also a velocity component within the scope window or lens 29 surface plane in the tangential direction of the surface of the window or lens 29, which facilitates the formation of vortex flow on the surface of the window or lens 29 to enhance cleaning efficiency. In one or more embodiments, the axial fluid flow velocity may be used for irrigation.

One or more embodiments of a nozzle 33 may be either an individual component or part of the outer tube 115 at the tube tip.

Figure 14:
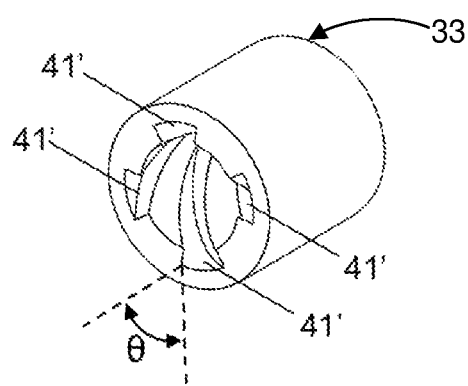
FIG. 14 shows at least one embodiment of a nozzle with helical grooves and one or more dimension details thereof in accordance with one or more aspects of the present disclosure.
Figure 15:
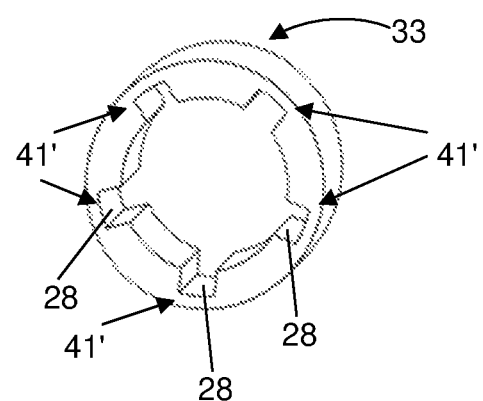
FIG. 15 shows at least one embodiment of a nozzle with grooves parallel or substantially parallel to a nozzle axis in accordance with one or more aspects of the present disclosure.

As best shown in FIGS. 14-15, embodiments that use one or more helical grooves 41' may employ different helical groove designs. For example, the number of grooves is preferably equal to or greater than ($\geq$) 1. The embodiment of FIG. 14 shows four grooves 41', for example, whereas the embodiment of FIG. 15 shows five grooves 41', as another example. By way of another example, an angle, $\theta$, of the grooves with respect to the nozzle axial direction as shown in FIG. 14 may meet the following equation or condition: $0° \leq \theta < 90°$. The number of grooves and one or more of the dimensions or any other structural detail of the helical groove(s) 41' may be variable, and may change from one embodiment to another embodiment and/or from one groove 41' to another groove 41'. For example, FIG. 15 shows an embodiment example of a nozzle design for the case where $\theta = 0°$, at which the helical grooves 41' become straight and parallel to the nozzle axis. In one or more embodiments, the angle may be different for different grooves 41', or a predetermined number of grooves 41' may use one angle whereas a predetermined number of other grooves 41' may use a different angle.

One or more catheter features discussed in U.S. Pat. Pub. 2019/0313975, published on Oct. 17, 2019 and filed on Apr. 17, 2018, the disclosure of which is incorporated by reference herein in its entirety, may be used with one or more embodiments or one or more features of the present disclosure. Additionally or alternatively, one or more catheter features discussed in U.S. Pat. Pub. No. 2017/0360398, published on Dec. 21, 2017 and filed on Jun. 20, 2017, the disclosure of which is incorporated by reference herein in its entirety, may be used with one or more embodiments or one or more features of the present disclosure.

Figure 16:
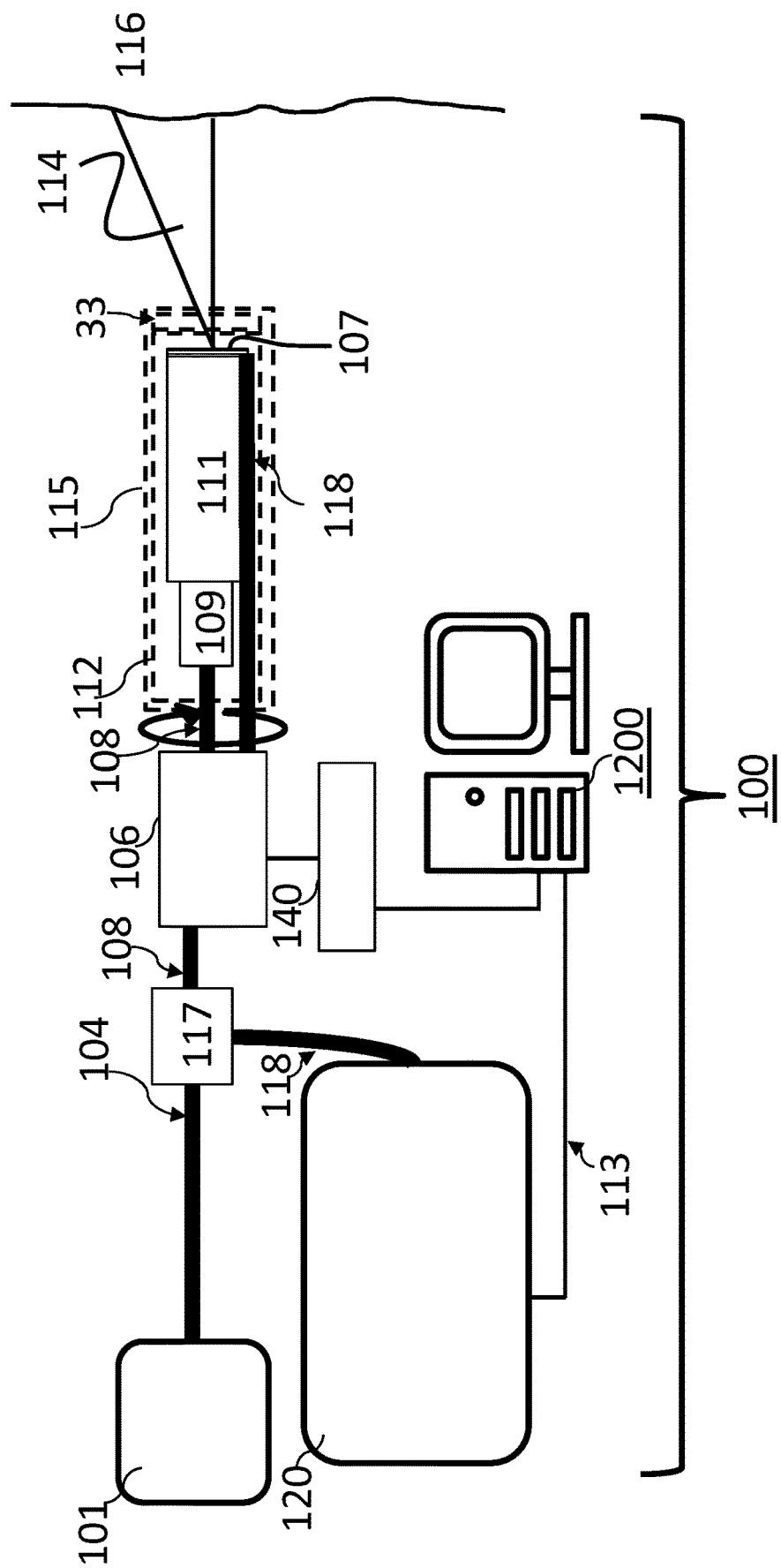
FIG. 16 is a diagram of at least one embodiment of an SEE system that may use one or more embodiments of cleaning technique(s) and/or structure(s) in accordance with one or more aspects of the present disclosure.

One or more embodiment examples of apparatuses or systems may use the cleaning feature(s), function(s), or technique(s) and/or the cleaning structure(s) features discussed herein. By way of at least one non-limiting, non-exhaustive embodiment example, FIG. 16 shows a ("SEE") system 100 (also referred to herein as "system 100" or "the system 100") which operates to utilize a SEE technique with one or more of the cleaning feature(s), function(s), or technique(s) and/or the cleaning structure(s) technology discussed herein for optical probe applications in accordance with one or more aspects of the present disclosure (as aforementioned, the one or more cleaning structure(s), feature(s), function(s), and/or technique(s) are not limited to SEE applications and may be employed in any of the aforementioned applications or in other imaging applications, devices, systems, methods, and/or storage mediums). As shown in FIG. 16, light emitted by a white light source 101 is transmitted by at least one illumination light transmission fiber 104 and/or 108 (fibers 104, 108 being non-limiting, non-exhaustive examples of at least one signal transmitting element and/or of at least one rotatable signal transmitting element in one or more embodiments) and is incident on a probe portion 112 (also referred to herein as "probe section 112" or "the probe 112"; another non-limiting, non-exhaustive example of at least one signal transmittal element and/or of at least one rotatable signal transmitting element in one or more embodiments) via a rotary joint or junction (hereinafter, RJ"; another non-limiting, non-exhaustive example of at least one signal transmittal element; a rotary or rotating portion of the RJ being another non-limiting example of at least one rotatable signal transmitting element in one or more embodiments) 106 (e.g., the at least one fiber(s) 104 and/or 108 may extend through the RJ 106 and into the probe portion 112 (e.g., the at least one fiber(s) 104 and/or 108 may be connected to and through a proximal side of the probe 112 via a signal transmitting connector/connection)) and/or may be incident on a probe portion (e.g., the probe portion 112"; another non-limiting, non-exhaustive example of at least one signal transmittal element and/or of at least one rotatable signal transmitting element in one or more embodiments) such that the light passes through a window or a lens of the probe portion 112 (another non-limiting, non-exhaustive example of at least one signal transmittal element and/or of at least one rotatable signal transmitting element in one or more embodiments) and such that one or more cleaning structure(s) or technique(s) may be employed at the end of the probe portion 112 shown diagrammatically in the box 33 (e.g., where a nozzle or other cleaning structure (e.g., one or more of the aforementioned nozzles 33 or a nozzle having any other structure(s) or feature(s) discussed herein; another non-limiting, non-exhaustive example of at least one signal transmittal element and/or of at least one rotatable signal transmitting element in one or more embodiments) discussed herein may be attached to the probe portion 112). An outer tube 115 (another non-limiting, non-exhaustive example of at least one signal transmittal element and/or of at least one rotatable signal transmitting element in one or more embodiments) may be used with the probe portion 112 and the cleaning means (shown diagrammatically by box 33; e.g., one or more of the aforementioned nozzles 33 or a nozzle having any other structure(s) or feature(s) discussed herein) in accordance with one or more embodiment discussed herein. Additionally or alternatively, the light emitted by the white light source 101 may be transmitted by the at least one illumination light transmission fiber 104, 108 and is incident on the probe 112 via a deflecting or deflected section 117 and via the RJ 106 as shown in FIG. 16, for example. In one or more embodiments (see e.g., as discussed in at least U.S. patent application Ser. No. 16/184,832, filed Nov. 8, 2018, the disclosure of which is incorporated by reference herein in its entirety) a length of an optical fiber 108 (e.g., a first stationary fiber) may extend from the deflecting or deflected section 117 and connect to one side of the RJ 106, and a length of a different optical fiber 108 (e.g., that operates to receive light that is coupled from the RJ 106 to the different optical fiber 108 and that operates to rotate along with the at least one cleaning means 33 (e.g., a nozzle or cleaning mechanism using one or more features discussed herein; one or more of the aforementioned nozzles 33; etc.) the position of which is shown diagrammatically by the dashed box in FIG. 16, the probe 112, the tube 115, etc.) may extend from the other side of the RJ 106 to the probe 112. In one or more embodiments of the probe 112, the white light beam is incident on a spacer 111 via a gradient-index lens (hereinafter, GRIN lens) 109. A diffraction grating (hereinafter, diffractive element) 107 is provided at the leading end portion of the spacer 111 (e.g., the GRIN lens 109 and the diffraction grating 107 are located on opposite sides of the spacer 111), and as the white light beam is incident on this diffractive element 107, a spectral sequence 114 is formed on a target (e.g., an object, a specimen, a subject, a patient, etc.) 116. In one or more embodiments, the probe 112 may not include the spacer 111, and the GRIN lens 109 may be connected to the diffractive element 107 to permit the spectral sequence 114 to be formed on the target 116. Reflected light from the spectral sequence 114 (e.g., light from the spectral sequence 114 that is formed on, and is reflected by, the target 116; light that is reflected by the target 116; etc.) is taken in by a detection fiber or cable 118. Although one detection fiber 118 is illustrated in FIG. 16, a plurality of detection fibers may be used. In one or more embodiments, the detection fiber 118 may extend to and/or near the end of the probe 112 (e.g., at the distal end of the probe 112). For example, in the system 100 of FIG. 16, the detection fiber 118 may have a detection fiber portion (see fiber 118 extending through the probe 112 in FIG. 16) that extends from or through the RJ 106 through, and to (e.g., connected to and through a proximal side of the probe 112 via a signal transmitting connector/connection as shown in FIG. 16) and/or near (e.g., adjacent to the end of the probe 112, about the end of the probe 112, near the end of the probe 112 closest to the target 116, etc.) the end of, the probe 112. The light taken in by the detection fiber 118 is separated into spectral components and detected by at least one detector, such as, but not limited to, a spectrometer 120 (and/or one or more components thereof as discussed herein), provided at the exit side of the detection fiber 118. In one or more embodiments, the end of the detection fiber 118 that takes in the reflected light may be disposed on or located near at least one of: the diffraction grating 107, the end of the spacer 111, the end of the probe 112, etc. Additionally or alternatively, the reflected light may be passed at least one of: through the probe 112, through the GRIN lens 109, through the rotary junction 106, through the tube 115, etc., and the reflected light may be passed, via a deflecting or deflected section 117 (discussed below), to the spectrometer 120. As shown in FIG. 16, as the portion extending from the RJ 106 to the probe 112 is rotated about the rotational axis extending in the longitudinal direction of the probe 112, the spectral sequence 114 moves in a direction orthogonal to the spectral sequence 114, and reflectance information in two-dimensional directions may be obtained. Arraying these pieces (e.g., the reflectance information in two-dimensional directions) of information makes it possible to obtain a two-dimensional image.

In other embodiments, the apparatus or system may be, for example, a chip-on-tip system. Thus, as shown in FIG. 2, the scope 112, may include an imaging sensor, such as, but not limited to, a charge coupled device (CCD), a complementary metal-oxide semiconductor (CMOS) sensor, or a light emitting diode (LED), placed at the distal end of the endoscope or probe 112. The signal from this sensor may be sent through the scope 112 or transmitted wirelessly to the computer 1200, 1200' (or any other processor or computer as discussed herein).

Preferably, in one or more embodiments including the deflecting or deflected section 117 (best seen in FIG. 16), the deflected section 117 operates to deflect the light from the light source 101 to the probe 112, and then send light received from the probe 112 towards at least one detector (e.g., the spectrometer 120, one or more components of the spectrometer, another type of detector, etc.). In one or more embodiments, the deflected section (e.g., the deflected section 117 of the system 100 as shown in FIG. 16) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 117, the rotary junction 106, the cleaning means or structure 33 (e.g., one or more of the aforementioned nozzles 33; a nozzle having any other structure(s) or feature(s) discussed herein; a cleaning means or structure having any structure(s) or feature(s) discussed herein; etc.), the tube 115, and/or the probe 112 (and/or one or more components thereof).

While not limited to such arrangements, configurations, devices or systems, one or more embodiments of the methods discussed herein may be used with a SEE probe as aforementioned, such as, but not limited to, for example, the system 100 (see FIG. 16), etc. In one or more embodiments, one user may perform the method(s) discussed herein. In one or more embodiments, one or more users may perform the method(s) discussed herein.

The devices and/or systems, such as, but not limited to, the system 2, the system 10, the system 100, etc.), etc., may include or be connected to a broadband light source 101

(best shown in FIG. 16 for the system 100). The broadband light source 101 may include a plurality of light sources or may be a single light source. The broadband light source 101 may include one or more of a laser, an organic light emitting diode (OLED), a light emitting diode (LED), a halogen lamp, an incandescent lamp, supercontinuum light source pumped by a laser, and/or a fluorescent lamp. The broadband light source 101 may be any light source that provides light which may then be dispersed to provide light which is then used to for spectral encoding of spatial information. The broadband light source 101 may be fiber coupled or may be free space coupled to the other components of the apparatus and/or system 100 or any other embodiment discussed herein.

As best seen in FIG. 16, the system 100 (or any other apparatus or system discussed herein) may include a rotary junction 106 (see e.g., the systems discussed herein, including, but not limited to, the system 2, the system 10, the systems using one or more features of FIGS. 1-15 or any other figure discussed herein, etc.). The connection between the light source 101 and the rotary junction 106 may be a free space coupling or a fiber coupling via fiber 104. The rotary junction 106 may supply just illumination light via the rotary coupling or may supply one or more of illumination light, power, and/or sensory signal lines.

As best seen in FIG. 16, the rotary junction 106 may couple the light to a first waveguide 108. In at least one embodiment, the first waveguide 108 is a single mode fiber, a multimode fiber, or a polarization maintaining fiber.

In one or more embodiments, the first waveguide 108 may be coupled to an optical apparatus and/or system that operates as an imager or imaging device, such as, for example the probe 112 (also referred to herein as an imager, imaging device or system, and/or optical apparatus and/or system). The optical apparatus and/or system (or the imager), or the probe 112, may include one or more optical components, that refract, reflect, and disperse the light from the first waveguide 108 to form at least one line of illumination light 114 (e.g., additionally or alternatively, in one or more embodiments, an imaging device or probe 112 in an apparatus or system (e.g., a SEE system, an endoscope system, another catheter-related system, any other type of imaging system, etc.) may form a plurality of illumination lines, such as, but not limited to, from three (3) wavelength ranges in a spectrum (such as, but not limited to, in the following colors: Red (R), Green (G), Blue (B), etc.), and may overlap the plurality of illumination lines (e.g., the three (3) illumination lines) in the same or substantially the same position on the target, the object, the sample or the patient 116) on a sample, an object or a patient 116 (e.g., a predetermined area in the patient, a predetermined area in and/or on a target, through the patient, through the target, etc.). In an embodiment, the line of illumination light 114 is a line connecting focal points for a wavelength range as the illumination light exits the optical apparatus and/or system (or the imager, the imaging device, or the probe) 112, the wavelength range being determined by the light source 101. In another embodiment, the spectrometer 120 may further limit the wavelength range by only using information from specified wavelengths of interest. In another embodiment, the line of illumination light 114 is a line formed by the illumination light as the illumination light intersects a surface of the target, the sample, the object or the patient 116 for the range of wavelengths that are detected by the spectrometer 120. In another embodiment, the line of illumination light 114 is a line of illumination light in a wavelength range formed on a specific image plane which is determined by the detection optics. In one or more embodiments, only some of the points on the image line may be in focus while other points on the image line may not be in focus. The line of illumination light 114 may be straight or curved.

In an alternative embodiment, the optical apparatus and/or system (or the imager or imaging device) 112 may partially collimate the light from the waveguide 108 such that the light is focused onto the sample, the object or the patient 116 but the light is substantially collimated at a dispersive optical element such as a grating.

The apparatus (such as the system 2, 10, 100, any other apparatus/system discussed herein, etc.) may include a detection waveguide 118. The detection waveguide 118 may be a multimode fiber, a plurality of multimode fibers, a fiber bundle, a fiber taper, or some other waveguide. In one or more embodiments, preferably the detection waveguide 118 comprises a plurality of detection fibers (e.g., forty-five (45) fibers, sixty (60) fibers, in a range of 45-60 fibers, less than 45 fibers, more than 60 fibers, etc.). The plurality of detection fibers of the detection waveguide 118 may be spaced apart and located around the periphery (e.g., inside the periphery, around a border of the periphery, etc.) of the imaging device or the probe 112. The detection waveguide 118 gathers light from the target, the sample, the object and/or the patient 116 which has been illuminated by light from the optical apparatus and/or system (or the imager or the imaging device, or the probe) 112. The light gathered by the detection waveguide 118 may be reflected light, scattered light, and/or fluorescent light. In one embodiment, the detection waveguide 118 may be placed before or after a dispersive element of the optical apparatus and/or system, or the probe, 112. In one embodiment, the detection waveguide 118 may be covered by the dispersive element of the optical apparatus and/or system, or the probe, 112, in which case the dispersive element may act as wavelength-angular filter. In another embodiment, the detection waveguide 118 is not covered by the dispersive element of the optical apparatus and/or system, imager or imaging device 112. The detection waveguide 118 guides detection light from the target, the sample, the object and/or the patient 116 to the spectrometer 120.

The spectrometer 120 may include one or more optical components that disperse light and guide the detection light from the detection waveguide 118 to one or more detectors. The one or more detectors may be a linear array, a charge-coupled device (CCD), a plurality of photodiodes or some other method of converting the light into an electrical signal. The spectrometer 120 may include one or more dispersive components such as prisms, a prisms, gratings, or grisms. The spectrometer 120 may include optics and opto-electronic components which allow the spectrometer 120 to measure the intensity and wavelength of the detection light from the target, the sample, the object and/or the patient 116. The spectrometer 120 may include an analog to digital converter (ADC). The separated illumination lights (e.g., illumination light 114) are emitted from a surface of the diffraction grating 107 to illuminate the object, and reflected lights (returned lights) from the object pass through the diffraction grating 107 again and are delivered to the spectrometer 120 by the detection fiber (DF) 118. In some embodiments, the reflected lights (returned lights) from the patient, subject, target, object (e.g., the object 116), etc. are delivered to the spectrometer 120 by the detection fiber (DF) 118 without first passing through the diffraction grating 107.

The spectrometer 120 may transmit the digital or analog signals to a processor or a computer such as, but not limited to, an image processor, a processor or computer 1200, 1200' (see e.g., FIGS. 16 and 18-19), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the spectrometer 120. The image processor may include one or more of a CPU, DSP, FPGA, ASIC, or some other processing circuitry. The image processor may include memory for storing image, data, and instructions. The image processor may generate one or more images based on the information provided by the spectrometer 120. A computer or processor discussed herein, such as, but not limited to, the system 2, the computer 1200, the computer 1200', the image processor, may also include one or more components further discussed herein below (see e.g., FIGS. 18-19).

One or more components of the apparatus and/or system (such as the system 2, 10, 100, etc.) may be rotated via the rotary junction 106, or oscillated so as to scan a line of illumination light 114 so as to create a 2D array of illumination light. A 2D image may be formed by scanning a spectrally encoded line from the optical apparatus and/or system, the imager or imaging device, or the probe, 112 across the target, the sample, the object and/or the patient 116. The apparatus and/or system (such as the system 2, 10, 100, etc.) may include an additional rotary junction that couples the light from the detection fiber 118 to the spectrometer 120. Alternatively, the spectrometer 120 or a portion of the spectrometer 120 may rotate with the fiber 118. In an alternative embodiment, there is no rotary junction 106 and the light source rotates with the fiber 108. An alternative embodiment may include an optical component (mirror) after a dispersive element in the optical system or imager, or the probe, 112 which rotates or scans the spectrally encoded line of illumination light across the target, the sample, the object and/or the patient 116 substantially perpendicular to the spectrally encoded line of illumination light 114 in a linear line to produce a 2D image or circumferentially in a circle so as to produce a toroidal image. Substantially, in the context of one or more embodiments of the present disclosure, means within the alignment and/or detection tolerances of the apparatus and/or system (such as the system 100 or any other system discussed herein) and/or any other system being discussed herein may be utilized or accounted for. In an alternative embodiment, there is no rotary junction 106 and an illumination end of the optical apparatus and/or system or the imager, or the probe, 112 is scanned or oscillated in a direction perpendicular to the illumination line. The cleaning means or structure (e.g., a nozzle) may be positioned in numerous ways, including, but not limited to, the ways shown in FIGS. 1-16.

In one or more alternative embodiments, a dispersive element 107 (i.e., a diffraction grating) may be used in the optical apparatus and/or system, or the probe, 112 as shown, respectively, in FIG. 16. In one or more embodiments (best seen in FIG. 16), light that has been emitted from the core of the end portion of the illumination optical fiber or the first waveguide 108 (e.g., an illumination optical fiber or the first waveguide 108 may be connected to and through a proximal side of the probe 112 via a signal transmitting connector/ connection as shown in FIG. 16) may enter a spacer 111 via a refractive-index distribution lens (hereinafter referred to as a gradient index (GRIN) lens") 109. The diffraction grating 107 is formed at the tip portion of the spacer 111 as shown in FIG. 16, and a spectral sequence 114 is formed on the target, the subject, object or sample 116 by a light flux (e.g., of white light) entering the diffraction grating 107. FIG. 16 illustrates an embodiment of apparatus and/or system 100 including a spectrometer, and a deflecting or deflected section 117 such that the cable or fiber 104 and/or the cable or fiber 108 connecting the light source 101 to the rotary junction 106 and/or the optical apparatus and/or system (or the probe) 112 and the cable or fiber 118 connecting the spectrometer 120 to the rotary junction 106 and/or the optical apparatus and/or system or imager (or the probe) 112 pass through, and are connected via, the deflected section 117 (discussed further below).

Figure 18:
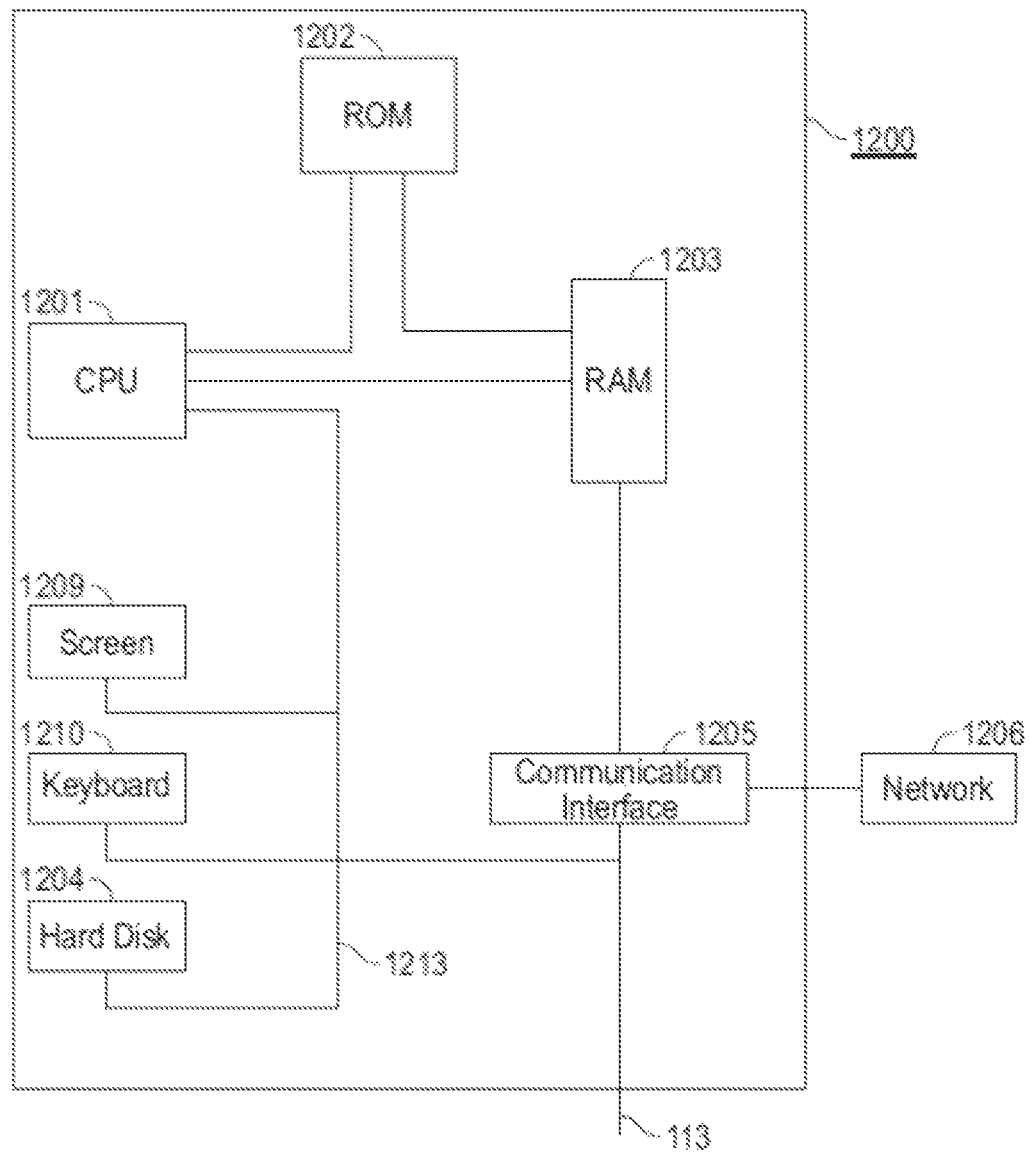
FIG. 18 shows a schematic diagram of an embodiment of a computer that may be used with one or more embodiments of an imaging apparatus or system one or more methods discussed herein in accordance with one or more aspects of the present disclosure.
Figure 19:
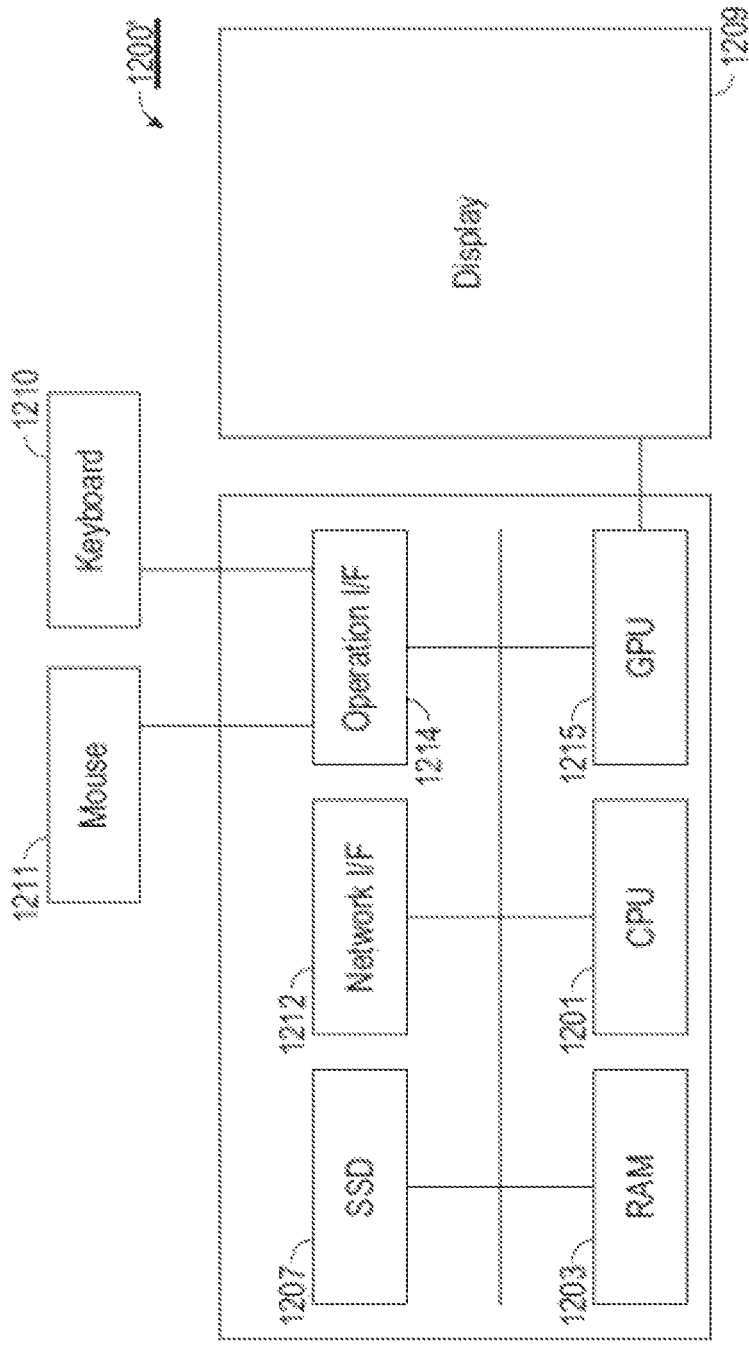
FIG. 19 shows a schematic diagram of another embodiment of a computer that may be used with one or more embodiments of an imaging apparatus or system or methods discussed herein in accordance with one or more aspects of the present disclosure.

In at least one embodiment, a console or computer 1200, 1200' operates [0076] to control motions of the RJ 106 via a Motion Control Unit (MCU) or a motor 140 (a non-limiting embodiment example of a driving motor), acquires intensity data from the detector(s) in the spectrometer 120, and displays the scanned image (e.g., on a monitor or screen such as a display, screen or monitor 1209 as shown in the console or computer 1200 of any of FIG. 16 and FIG. 18 and/or the console 1200' of FIG. 19 as further discussed below). In one or more embodiments, the MCU or the motor 140 operates to change a speed of a motor of the RJ 106 and/or of the RJ 106. The motor may be a stepping or a DC servo motor to control the speed and increase position accuracy. In one or more embodiments, the deflection or deflected section 117 may be at least one of: a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc. In one or more other embodiments, the rotary junction 106 may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 108 (e.g., single mode fiber, a GRIN lens, a spacer and the grating on the polished surface of the spacer, etc.). In one or more embodiments, a scope may refer to the illumination portion which, for example, may be enclosed and protected by a drive cable, a tube, and detection fibers (e.g., multimode fibers (MMFs)) around the tube. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 118, the spectrometer 120, the computer 1200, the computer 1200', etc. The detection fibers, such as the detection fiber(s) 118, may surround the illumination fiber, such as the IF 108, and the detection fibers may or may not be covered by the grating, such as the grating 107.

In an embodiment, the first waveguide 108 may be single mode fiber. In an alternative embodiment, the first waveguide 108 may be a multimode fiber or a double clad fiber. In an embodiment, the second waveguide 118 may be a multi-mode fiber a single mode fiber, or a fiber bundle.

In an alternative embodiment, the first waveguide 108 may be an inner core of a double-clad fiber, while the second waveguide 118 may be between the inner core and the outer cladding of the double clad fiber. If a double clad fiber is used, an alternative embodiment may include an optical coupler for guiding illumination light to the inner core, and the optical coupler may also receive detection light from the outer waveguide which is then guided to the spectrometer 120.

In one or more embodiments, a SEE probe may include the illumination fiber(s) 104 and/or 108, the diffraction grating 107 and the detection fiber 118, and the illumination fiber(s) 104 and/or 108, the diffraction grating 107 and the detection fiber 118 may be housed by a metal or plastic tube to enhance the SEE probe's robustness for rotational motions and external stress by insertion. The SEE probe may further include a lens at the distal end of the probe, which may be located after the diffraction grating 107 (not shown), or between the diffraction grating 107 and the illumination fiber 108 (see e.g., the lens or prism 109 as shown in FIG. 16 and as discussed further below), or between the diffraction grating 107 and the detection fiber 118. In one or more embodiments, a SEE probe is incorporated with the motor or MCU 140 at a proximal side, which enables the SEE probe to scan in a horizontal direction, for example, with a periodical arc motion. In one or more embodiments, the motor 140 may be a rotational motor to achieve, for example, circumferential viewing. In some embodiments, the systems 2, 10, 100, or any other system discussed herein, may include one or more rotary junctions (not shown) that are configured to rotate the illumination fiber 108 or the illumination fiber 108 and the detection fiber 118. In at least one embodiment, the detection fiber 118 may be coupled with the spectrometer 120 including a diffraction grating and the at least one detector of the spectrometer 120.

The output of the one or more components of any of the systems discussed herein may be acquired with the at least one detector and/or the spectrometer 120, e.g., such as, but not limited to, photodiodes, Photomultiplier tube(s) (PMTs), line scan camera(s), or multi-array camera(s). Electrical analog signals obtained from the output of the system 100 and/or the spectrometer thereof are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector and/or the spectrometer 120 comprises three detectors configured to detect three different bands of light. In yet other embodiments, the spectrometer 120 is configured to generate three 2D images from three different bands of light (e.g., red, green, and blue) where these three 2D images may be combined to form a single image having color information. In yet other embodiments, multiple spectrometers 120 may be used to generate different 2D images from the three different bands of light.

Figure 17:
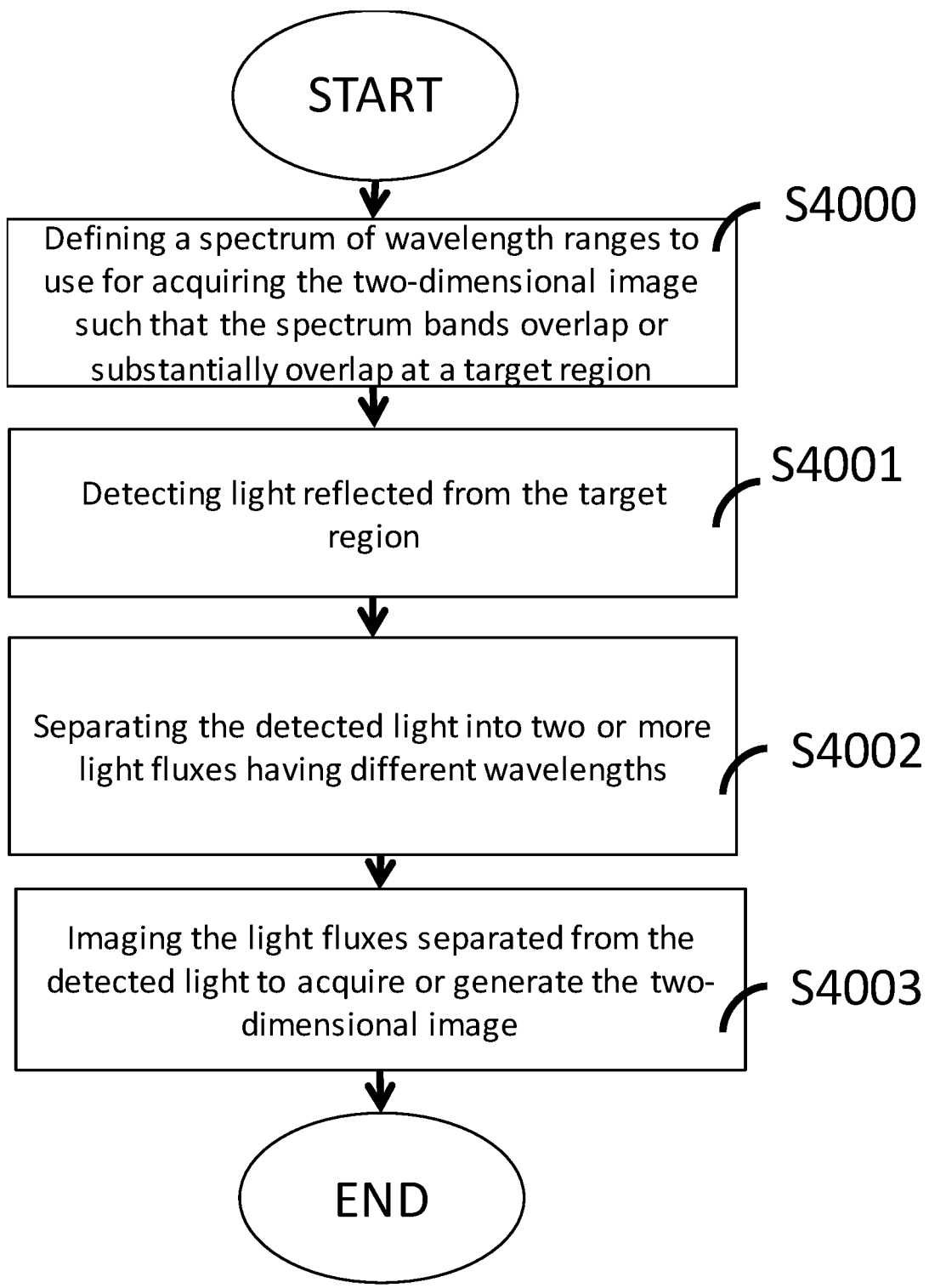
FIG. 17 is a flow diagram showing a method of performing an imaging technique in accordance with one or more aspects of the present disclosure.

In accordance with at least one aspect of the present disclosure and as aforementioned, one or more methods for performing tissue characterization when using an imaging apparatus or system are provided herein. By way of at least one embodiment, a method for characterizing tissue using a SEE system may include one or more of the following: (i) setting object information; (ii) designating one or more imaging conditions; (iii) start imaging; (iv) coordinating intensities to construct a SEE image; (v) determining tissue type; (vi) displaying tissue type on a center (or other predetermined location) of a scanned tissue image; and (vii) determining whether to change a region of interest (ROI); (viii) if "Yes" the prior step, then adjusting a measuring position toward the center of the image and then determining whether to end the exam; if "No", repeating the prior step, and if "Yes", end the process), or if "No" in the prior step of determining whether to change the ROI, then keep displaying the scanned tissue image and tissue type and then repeat the step of determining whether to change the ROI. By way of at least another embodiment, a method may include one or more steps for performing imaging. By way of at least one embodiment example shown in FIG. 17, a method may include the following imaging control steps (or any other catheter methods or structure discussed in U.S. Pat. App. Ser. No. 62/634,011, filed on Feb. 22, 2018, the disclosure of which is incorporated by reference herein in its entirety, any details as discussed in U.S. patent application Ser. No. 16/270,304, filed Feb. 7, 2019, the disclosure of which is incorporated by reference herein in its entirety, and/or any other fluid details disclosed in U.S. patent application Ser. No. 15/955,574, filed on Apr. 17, 2018, the disclosure of which is incorporated by reference herein in its entirety). For example, as shown in FIG. 17, in at least one embodiment: the method(s) may include one or more of the following: (i) defining a spectrum of wavelength ranges to use for acquiring the image such that the spectrum bands overlap or substantially overlap on a sample or target (see step S4000 in FIG. 17); (ii) detecting light reflected from the target region (see step S4001 in FIG. 17); (iii) separating the detected light into two or more light fluxes having different wavelengths (see step S4002 in FIG. 17); and (iv) imaging the light fluxes separated from the detected light to acquire or generate the black and white and/or color image (see step S4003 in FIG. 17). One or more methods may further include at least one of: using a probe grating to generate the spectrum bands that overlap or substantially overlap on the target region; and optimizing the probe grating so that a diffraction efficiency is high within the wavelength ranges.

In one or more embodiments, an imaging probe may be connected to one or more systems (e.g., the system 100, the system 10, the system 2, the apparatus or system using one or more features of any of FIGS. 1-15, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a tube, and detection fibers (e.g., multimode fibers (MMFs)) around the tube. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors, a spectrometer 120, etc.), the computer 1200, the computer 1200', etc. The detection fibers may surround the illumination fiber, and the detection fibers may or may not be covered by a grating, a spacer, a lens, an end of a probe or catheter, etc.

In one or more embodiments, a probe may be connected to one or more systems (e.g., the system 2, the system 10, the system 100, or any other system discussed herein, etc.) with a connection member or interface module. For example, when the connection member or interface module is a rotary junction for either a SEE probe, an endoscope, or other catheter-related system, the rotary junction may be at least one of: a contact rotary junction, a lenseless rotary junction, a lens-based rotary junction, or other rotary junction known to those skilled in the art. The rotary junction may be a one channel rotary junction or a two channel rotary junction.

In one or more embodiments, a SEE probe may further include a lens located between the DG 107 and the sample, subject, or object (e.g., object 116). Preferably, in such an embodiment, the lens receives light from the fiber 108, DG 107 and/or the prism 109 (depending on which system, such as the system 2, the system 10, the system 100, etc., includes the lens) and passes the light therethrough towards the sample. After illuminating the sample, the light passes through the lens back towards the DG 107 and/or the prism 109 and into the fiber 118, and/or directly into the fiber 118. In one or more embodiments, the lens may or may not be tilted or angled. In one or more embodiments, the lens (or window) or other structure (e.g., a mirror, such as a dichroic mirror, glass, etc.) may be cleaned using one or more cleaning structure(s) or feature(s), function(s), or technique(s) discussed herein.

Unless otherwise discussed herein, like numerals indicate like elements. For example, while variations or differences exist between the systems, such as, but not limited to, the system 2, the system 10, the system 100, or any other system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 140, the at least one detector and/or the spectrometer 120, and/or one or more other elements of the system 100, may operate in the same or similar fashion to those like-numbered elements of one or more other systems, such as, but not limited to, the system 2, the system 10, or any other system discussed herein. In one or more embodiments, the computer, processor or console 1200, 1200' may be used in place of the any other computer or processor, such as, but not limited to, the computer or processor 2, the other computer, processor, or console 1200', 1200, etc. Those skilled in the art will appreciate that alternative embodiments of the system 2, the system 10, the system 100, any other system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 16 and one or more embodiments shown in any of FIGS. 1-15 and 18-19, for example, as discussed herein, there are similarities. Likewise, while the console or computer 1200 may be used in one or more systems (e.g., the system 10, the system 100, or any other system discussed herein, etc.), one or more other consoles or computers, such as the console or computer 1200', may be used additionally or alternatively.

There are many ways to compute intensity, viscosity, resolution (including increasing resolution of one or more images), creation of color images or any other measurement discussed herein, or to perform any imaging technique discussed herein, digital as well as analog. In at least one embodiment, a computer, such as the console or computer 1200, 1200', may be dedicated to control and monitor the imaging (e.g., SEE, endoscopy, other catheter-related imaging, etc.) devices, systems, methods and/or storage mediums described herein.

The electric signals used for imaging may be sent to one or more processors, such as, but not limited to, a computer 1200 (see e.g., FIG. 18), a computer 1200' (see e.g., FIG. 19), etc. as discussed further below, via cable(s) or wire(s), such as, but not limited to, the cable(s) or wire(s) 113 (see FIG. 18).

Light emitted by a white light source may be transmitted by an illumination light transmission fiber and may be incident on a probe portion. Additionally or alternatively, the light emitted by the white light source may be transmitted by the illumination light transmission fiber and may be incident on the probe portion via a deflecting or deflected section and via a rotary junction as aforementioned.

As aforementioned, a rotary junction for a probe may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the probe may be separate from the detection portion of the probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a tube, and detection fibers (e.g., multimode fibers (MMFs)) around the tube. Grating coverage is optional on the detection fibers (e.g., MMFs) for one or more applications. The illumination portion may be connected to a rotary joint and may be rotating continuously at video rate. In one or more embodiments, the detection portion operating to obtain the image data may include one or more of: a detection fiber, a spectrometer, a computer 1200, the computer 1200' (as discussed further below), etc.

Unless otherwise discussed herein, like numerals indicate like elements. For example, while the console or computer 1200 may be used in one or more systems or devices discussed herein, one or more other consoles or computers, such as the console or computer 1200', may be used additionally or alternatively, and any like-numbered elements thereof may operate in the same or similar fashion.

There are many ways to compute intensity, viscosity, resolution (including increasing resolution of one or more images), creation of color images or any other measurement discussed herein, digital as well as analog. In at least one embodiment, a computer, such as the console or computer 1200, 1200', may be dedicated to control and monitor the devices, systems, methods and/or storage mediums described herein.

In accordance with one or more aspects of the present disclosure, one or more methods for performing imaging may be performed using at least one cleaning structure or means and/or at least one cleaning feature, function, or technique as discussed herein.

Various components of a computer system 1200 are provided in FIG. 18. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., including but not limited to, being connected to the console, the probe, the cleaning structure(s) or means (e.g., a nozzle), any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, a system using at least one cleaning structure or means and/or at least one cleaning feature, function, or technique as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or sample characterization, diagnosis, evaluation and/or imaging. The system 1200 may further include one or more processors connected via a network connection (e.g., via network 1206). The CPU 1201 and any additional processor being used by the system 1200 may be located in the same telecom network or in different telecom networks (e.g., performing technique(s) discussed herein may be controlled remotely).

The I/O or communication interface 1205 provides communication interfaces to input and output devices, which may include a light source, a spectrometer, the communication interface of the computer 1200 may connect to other components discussed herein via line 113 (as diagrammatically shown in FIG. 18), a microphone, a communication cable and a network (either wired or wireless), a keyboard 1210, a mouse (see e.g., the mouse 1211 as shown in FIG. 19), a touch screen or screen 1209, a light pen and so on. The Monitor interface or screen 1209 provides communication interfaces thereto.

Any methods and/or data of the present disclosure, such as the methods for performing tissue or sample characterization, diagnosis, examination and/or imaging (including, but not limited to, increasing image resolution, performing imaging, cleaning a scope or other imaging component (e.g., a window, a mirror, or a lens of a scope or imaging device, glass, etc.) using at least one cleaning structure or means and/or at least one cleaning feature, function, or technique as discussed herein, etc.) as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 19), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 18. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 18) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 19. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a motor, a console, a cleaning structure(s) or means or any other component of the device(s) or system(s) discussed herein via the operation interface 1214 or the network interface 1212 (e.g., via a cable or fiber, such as the cable or fiber 113 as similarly shown in FIG. 18). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 1200, 1200', may communicate with an MCU, a cleaning structure(s) or means, etc. to perform imaging, cleaning an imaging component (e.g., a window or lens of a scope or imaging device, glass, a mirror, etc.) as desired, and to reconstruct an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9415550; 9,557,154 and arrangements and methods of facilitating photoluminescence imaging, such as those disclosed in U.S. Pat. No. 7,889,348 to Tearney et al. Other exemplary SEE systems are described, for example, in, U.S. Pat. Nos. 10,288,868; 10,261,223; 10,095,020; 9,869,854; 10,444,146; 9,869,820; 10,194,065; 10,321,810; 10,337,987; 10,371,614; 10,234,694; 10,222,607; 9,846,940; 10,401,610; 10,506,922; 10,357,160; 10,314,469; as well as U.S. Pat. Publication Nos. 2018/0088312; 2018/0214008; 2019/0174038; 2018/0084981; 2018/0120555; 2017/0290492; 2019/0172180; 2019/0231182; 2019/0162977; 2019/0150720; and 2019/0223706 and WO 2017/165511 A1, each of which patents, patent publications and application(s) are incorporated by reference herein in their entireties.

Similarly, the present disclosure and/or one or more components of devices, systems and storage mediums, and/or methods, thereof also may be used in conjunction with imaging catheter technologies and methods, such as, but not limited to, apparatuses, assemblies, systems, methods and/or storage mediums disclosed in at least, but not limited to: U.S. Pat. App. Ser. No. 62/634,011, filed on Feb. 22, 2018, the disclosure of which is incorporated by reference herein in its entirety, U.S. patent application Ser. No. 16/270,304, filed Feb. 7, 2019, the disclosure of which is incorporated by reference herein in its entirety, and/or any other details disclosed in U.S. patent application Ser. No. 15/955,574, filed on Apr. 17, 2018, the disclosure of which is incorporated by reference herein in its entirety. Additionally or alternatively, one or more catheter features discussed in U.S. Pat. App. Ser. No. 62/352,741, filed on Jun. 21, 2016, the disclosure of which is incorporated by reference herein in its entirety, and U.S. patent application Ser. No. 15/628,093, filed on Jun. 20, 2017, the disclosure of which is incorporated by reference herein in its entirety, may be used with one or more embodiments or one or more features of the present disclosure.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. An imaging apparatus comprising:
   a probe or scope having at least one signal transmitting element, a proximal end with a signal transmitting connector, and a distal end operating to communicate a probing signal with a specimen, object, or target at an imaging location to generate an image, the distal end of the probe or scope operating to connect to or include an imaging or observation window or lens; and
   a nozzle having a through hole or a center hole to expose the imaging or observation window or lens, and having one or more grooves that operate to clean the imaging or observation window or lens of the probe or scope at the imaging location, wherein:
   the nozzle further operates to provide one or more irrigation function(s) as well as operating to clean the imaging or observation window or lens of the probe or scope, and the nozzle further includes one or more channels to deliver and direct fluid(s) and/or cleaning fluid to provide both the window or lens cleaning and the one or more irrigation functions to increase procedural efficiency by eliminating device exchange(s), and
   the one or more channels include one or more exits or through holes extending from the channel to a distal end surface of the nozzle to provide outward and forward liquid flow channels for the one or more irrigation function(s), and the one or more channels:

(i) include one or more exits or through holes extending from the channel to an outer diameter surface of the nozzle to provide outward liquid flow channels for the one or more irrigation function(s), or (ii) extend from a proximal end surface of the nozzle to an outer diameter surface of the nozzle and operate to allow outwards flow for the one or more irrigation function(s).

2. The apparatus of claim 1, wherein one or more of the following occurs or exists:

(i) the apparatus further comprises an outer tube or outer tubular sheath;

(ii) the nozzle operates to expose the imaging or observation window or lens without impairing a field of view of the probe or scope;

(iii) the nozzle operates to position the probe or scope on both radial and axial directions relative to the outer tube or outer tubular sheath; and/or (iv) the one or more grooves are connected to an annular fluid delivery channel for cleaning of the window or lens, the annular fluid delivery channel being formed or defined between the probe or scope and the outer tube or outer tubular sheath and the annular fluid delivery channel operating to reduce or minimize an outer diameter of the apparatus.

3. The apparatus of claim 2, wherein one or more of the following occurs or exists:

(i) the one or more grooves are disposed on a proximal surface of the nozzle, or, in a case where the one or more channels extend from the proximal surface of the nozzle to the outer diameter surface of the nozzle and operate to allow outwards flow for the one or more irrigation function(s), the one or more grooves are disposed on the proximal surface of the nozzle;

(ii) the one or more grooves are perpendicular or substantially perpendicular to an axis extending along a length of the nozzle;

(iii) a proximal surface of the nozzle is perpendicular or substantially perpendicular to an axis extending along a length of the nozzle, or, in a case where the one or more channels extend from the proximal surface of the nozzle to the outer diameter surface of the nozzle and operate to allow outwards flow for the one or more irrigation function(s), the proximal surface of the nozzle is perpendicular or substantially perpendicular to an axis extending along a length of the nozzle;

(iv) the one or more grooves operate to become or define one or more closed channels for fluid(s) and/or cleaning fluid in a case where the nozzle is attached to a distal end of the outer tube and the scope or probe is inserted into the center hole or through hole of the nozzle;

(v) the one or more grooves on the nozzle are angled with respect to a radial direction of a proximal surface of the nozzle, or, in a case where the one or more channels extend from the proximal surface of the nozzle to the outer diameter surface of the nozzle and operate to allow outwards flow for the one or more irrigation function(s), the one or more grooves on the nozzle are angled with respect to a radial direction of the proximal surface of the nozzle;

(vi) the one or more grooves are arranged peripherally around the through hole or the center hole of the nozzle;

(vii) in a case where fluid(s) and/or cleaning fluid is delivered into and/or through the one or more grooves, the one or more grooves operate to guide the fluid(s) and/or the cleaning fluid in a direction to flush at least one surface of the window or lens and/or to facilitate formation of a vortex and/or swirl type of flow on the at least one surface of the window or lens to enhance cleaning efficiency;

(viii) the one or more grooves operate to guide fluid(s) and/or cleaning fluid in a direction to flush at least one surface of the window or lens tangentially and/or to facilitate formation of a vortex and/or swirl type of flow on the at least one surface of the window or lens to enhance cleaning efficiency; and/or (ix) the nozzle has one or more channels to deliver and direct fluid(s) and/or cleaning fluid to provide both window or lens cleaning and one or more irrigation functions to increase procedural efficiency by eliminating device exchange(s).

4. The apparatus of claim 3, wherein one or more of the following occurs or exists:

(i) the one or more grooves include a portion having at least one helical groove on an inner surface of the nozzle along the axial direction of the nozzle;

(ii) the one or more grooves include a portion having at least one helical groove on an inner surface of the nozzle along the axial direction of the nozzle, and the portion having the at least one helical groove communicates with the fluid channel between the outer tube and the probe or scope to deliver fluid(s) and/or cleaning fluid to at least one surface of the window or lens;

(iii) the one or more grooves include a portion having at least one helical groove on an inner surface of the nozzle along the axial direction of the nozzle, and the portion having the at least one helical groove operates to become or define one or more closed helical channels for fluid(s) and/or cleaning fluid in a case where the nozzle is attached to the distal end of the outer tube and the scope or probe is inserted into the center hole or the through hole of the nozzle;

(iv) the distal end surface of the nozzle is aligned flush with the at least one surface of the imaging or observation window or lens;

(v) the one or more grooves include a portion having at least one helical groove on an inner surface of the nozzle along the axial direction of the nozzle, the portion having the at least one helical groove operates to become or define one or more closed helical channels for fluid(s) and/or cleaning fluid in a case where the nozzle is attached to the distal end of the outer tube and the scope or probe is inserted into the center hole or the through hole of the nozzle, and, in a case where the fluid(s) and/or the cleaning fluid exits the one or more closed helical channels, a fluid flow velocity has a velocity component in the axial direction of the nozzle and also has a velocity component within a plane of the at least one surface of the window or lens in a tangential direction of the at least one surface of the window or lens, which facilitates a formation of a vortex flow on the at least one surface of the window or lens to enhance cleaning efficiency;

(vi) the nozzle is an individual component or a part of the outer tube at a tip of the tube; and/or (vii) the axial fluid flow velocity is used for irrigation.

5. The apparatus of claim 3, wherein one or more of the following occurs or exists:

(i) the number of the one or more grooves is $\geq 1$;

(ii) an angle, $\theta$, of the one or more grooves with respect to the axial direction of the nozzle meets the following equation or condition: $0° <= \theta < 90°$; and/or (iii) an angle, $\theta$, of the one or more grooves with respect to the axial direction of the nozzle meets the following equation or condition: the angle, θ, is =0°, at which the one or more grooves are straight and parallel or substantially parallel to the nozzle axis.

6. The apparatus of claim 1, wherein one or more of the following occurs or exists:
   (i) the at least one signal transmitting element is at least one rotatable signal transmitting element;
   (ii) the rotatable signal transmitting element of the probe includes or comprises fiber;
   (iii) the apparatus further includes a rotary joint or junction operating to transmit signals between a stationary portion of the apparatus and the at least one rotatable signal transmitting element of the probe or scope;
   (iv) the apparatus further includes a rotary joint or junction operating to transmit signals between a stationary portion of the apparatus and the at least one rotatable signal transmitting element of the probe or scope, and the apparatus further includes a driving motor that operates to one or more of:
      (a) drive the rotary joint or junction to drive rotational and/or axial movement of the probe or scope; and
      (b) control an angular position of the rotary joint or junction;
   (v) the apparatus further includes the stationary portion of the apparatus, wherein the stationary portion comprises a signal source and one or more signal detector subsystems; and/or
   (vi) the rotary joint or junction includes a stationary portion and a rotary portion.

7. The apparatus of claim 1, further comprising at least one processor that operates to: (i) acquire the probing signal to generate the image; and (ii) to control fluid(s) and/or cleaning fluid via the nozzle and/or the one or more grooves to clean the window or lens and/or to provide one or more irrigation function(s).

8. The apparatus of claim 1, wherein the imaging location is located inside the specimen, object, or target such that the cleaning occurs in situ in the specimen, object, or target.

9. The apparatus of claim 1, wherein the one or more channels one or more of the following:
   (i) communicate with the one or more grooves to deliver and direct the fluid(s) and/or cleaning fluid;
   (ii) extend, in a case where the one or more channels include the one or more exits or through holes extending from the channel to the outer diameter surface of the nozzle to provide outward liquid flow channels for the one or more irrigation function(s), from a proximal surface of the nozzle to the outer diameter surface of the nozzle and operate to allow outwards flow for the one or more irrigation function(s);
   (iii) have a plurality of portions that are differently sized and/or shaped to provide different flow velocities for the cleaning and/or the one or more irrigation function(s); and/or
   (iv) include, in a case where the one or more channels extend from the proximal surface of the nozzle to the outer diameter surface of the nozzle and operate to allow outwards flow for the one or more irrigation function(s), one or more exits or through holes extending from the channel to the outer diameter surface of the nozzle to provide outward liquid flow channels for the one or more irrigation function(s).

10. The apparatus of claim 1, wherein:
   (i) the number of the one or more grooves is ≥1; and
   (ii) a distance, D, between a center of each groove of the one or more grooves and an axis extending along a length of the nozzle meets the following equation: $0 < D < R + W/2$, where a width, W, of the each groove of the one or more grooves is $0 < W < R$, where R is a radius of the through hole or the center hole of the nozzle.

11. An imaging apparatus comprising:
   a probe or scope having at least one signal transmitting element, a proximal end with a signal transmitting connector, and a distal end operating to communicate a probing signal with a specimen, object, or target at an imaging location to generate an image, the distal end of the probe or scope operating to connect to or include an imaging or observation window or lens; and
   a nozzle having (i) a through hole or a center hole to expose the imaging or observation window or lens, (ii) a distal end surface that operates to be aligned flush with the at least one surface of the imaging or observation window or lens or to be perpendicular or substantially perpendicular to an axis extending along a length of the nozzle, and (iii) one or more grooves that operate to clean the imaging or observation window or lens of the probe or scope at the imaging location, the one or more grooves operating to become or define one or more channels for fluid(s) and/or cleaning fluid and the one or more grooves including a portion having at least one helical groove on an inner surface of the nozzle along an axial direction of the nozzle,
   wherein the at least one helical groove operates to become or further define the one or more channels for the fluid(s) and/or the cleaning fluid and/or the at least one helical groove communicates with the one or more fluid(s) and/or cleaning fluid channels between an outer tube and the probe or scope to deliver the fluid(s) and/or the cleaning fluid to at least one surface of the imaging or observation window or lens.

12. The imaging apparatus of claim 11, wherein one or more of the following occurs or exists:
   (i) the apparatus further comprises an outer tube or outer tubular sheath;
   (ii) the nozzle operates to expose the imaging or observation window or lens without impairing a field of view of the probe or scope;
   (iii) the nozzle operates to position the probe or scope on both radial and axial directions relative to the outer tube or outer tubular sheath; and/or
   (iv) the one or more grooves are connected to an annular fluid delivery channel for cleaning of the window or lens, the annular fluid delivery channel being formed or defined between the probe or scope and the outer tube or outer tubular sheath and the annular fluid delivery channel operating to reduce or minimize an outer diameter of the apparatus.

13. The imaging apparatus of claim 12, wherein one or more of the following occurs or exists:
   (i) the one or more grooves are disposed on a proximal surface of the nozzle;
   (ii) the one or more grooves are perpendicular or substantially perpendicular to the axis extending along the length of the nozzle;
   (iii) a proximal surface of the nozzle is perpendicular or substantially perpendicular to the axis extending along the length of the nozzle;
   (iv) the one or more grooves operate to become or define one or more closed channels for the fluid(s) and/or cleaning fluid in a case where the nozzle is attached to a distal end of the outer tube and the scope or probe is inserted into the center hole or through hole of the nozzle;

(v) the one or more grooves on the nozzle are angled with respect to a radial direction of a proximal surface of the nozzle;

(vi) the one or more grooves are arranged peripherally around the through hole or the center hole of the nozzle;

(vii) in a case where the fluid(s) and/or cleaning fluid is delivered into and/or through the one or more grooves, the one or more grooves operate to guide the fluid(s) and/or the cleaning fluid in a direction to flush at least one surface of the window or lens and to facilitate formation of a vortex and/or swirl type of flow on the at least one surface of the imaging or observation window or lens to enhance cleaning efficiency;

(viii) the one or more grooves operate to guide the fluid(s) and/or the cleaning fluid in a direction to flush the at least one surface of the imaging or observation window or lens tangentially and to facilitate formation of a vortex and/or swirl type of flow on the at least one surface of the imaging or observation window or lens to enhance cleaning efficiency; and/or (ix) the nozzle has one or more channels to deliver and direct the fluid(s) and/or the cleaning fluid to provide both window or lens cleaning and one or more irrigation functions to increase procedural efficiency by eliminating device exchange(s).

14. The imaging apparatus of claim 13, wherein one or more of the following occurs or exists:

(i) the at least one helical groove operates to become or define one or more closed helical channels for the fluid(s) and/or the cleaning fluid in a case where the nozzle is attached to a distal end of the outer tube and the scope or probe is inserted into the center hole or the through hole of the nozzle;

(ii) the portion of the one or more grooves having the at least one helical groove operates to become or define one or more closed helical channels for the cleaning fluid in a case where the nozzle is attached to a distal end of the outer tube and the scope or probe is inserted into the center hole or the through hole of the nozzle, and, in a case where the cleaning fluid exits the one or more closed helical channels, a fluid flow velocity has a velocity component in the axial direction of the nozzle and also has a velocity component within a plane of the at least one surface of the window or lens in a tangential direction of the at least one surface of the window or lens, which facilitates a formation of a vortex flow on the at least one surface of the window or lens to enhance cleaning efficiency;

(iii) the nozzle is an individual component or a part of the outer tube at a tip of the tube; and/or (iv) the axial fluid flow velocity is used for irrigation.

15. The imaging apparatus of claim 13, wherein one or more of the following occurs or exists:

(i) the number of the one or more grooves is $\geq 1$;

(ii) an angle, $\theta$, of the one or more grooves with respect to the axial direction of the nozzle meets the following equation or condition: $0° \leq \theta < 90°$; and/or an angle, $\theta$, of the one or more grooves with respect to the axial direction of the nozzle meets the following equation or condition: the angle, $\theta$, is $=0°$, at which the one or more grooves are straight and parallel or substantially parallel to the nozzle axis.

\* \* \* \* \*